(12) United States Patent
Wagner et al.

(10) Patent No.: US 9,821,290 B2
(45) Date of Patent: Nov. 21, 2017

(54) DEVICES AND METHODS FOR PARAHYDROGEN INDUCED POLARIZATION

(71) Applicant: Cedars-Sinai Medical Center, Los Angeles, CA (US)

(72) Inventors: Shawn Wagner, Altadena, CA (US); Jose Agraz, Brea, CA (US); Debiao Li, South Pasadena, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 14/426,454

(22) PCT Filed: Sep. 6, 2013

(86) PCT No.: PCT/US2013/058625
§ 371 (c)(1),
(2) Date: Mar. 6, 2015

(87) PCT Pub. No.: WO2014/039907
PCT Pub. Date: Mar. 13, 2014

(65) Prior Publication Data
US 2015/0217262 A1 Aug. 6, 2015

Related U.S. Application Data

(60) Provisional application No. 61/698,488, filed on Sep. 7, 2012.

(51) Int. Cl.
*B01J 19/08* (2006.01)
*G01R 33/28* (2006.01)
*A61K 49/06* (2006.01)
*C07C 69/67* (2006.01)
*G01R 33/56* (2006.01)

(52) U.S. Cl.
CPC ............. *B01J 19/088* (2013.01); *A61K 49/06* (2013.01); *C07C 69/67* (2013.01); *G01R 33/282* (2013.01); *B01J 2219/0805* (2013.01); *G01R 33/5601* (2013.01)

(58) Field of Classification Search
CPC ........ A61L 49/06; B01J 19/08; B01J 19/2415
See application file for complete search history.

(56) References Cited

U.S. PATENT DOCUMENTS

| | | | |
|---|---|---|---|
| 5,425,104 A | 6/1995 | Shennib | |
| 7,255,833 B2 * | 8/2007 | Chang | B01J 19/0093 422/417 |
| 8,766,633 B2 * | 7/2014 | Bhattacharya | A61B 5/055 324/307 |
| 2011/0274626 A1 | 11/2011 | Duckett et al. | |

OTHER PUBLICATIONS

International Search Report and Written Opinion for International Application No. PCT/US13/58625, dated Feb. 18, 2014, 11 pages.
IPRP for International Application No. PCT/US13/58625, dated Feb. 18, 2014, 10 pages.
Hovener, J. B. et al., Pasadena hyperpolarization of 13C biomolecules: equipment design and installation, MAGMA, 2009, 22:111-121.
Waddell, K.W. et al., In Situ detection of PHIP at 48 mT: Demonstration using a centrally controlled polarizer, JACS, 2011, 133:97-101.

* cited by examiner

*Primary Examiner* — Michael G Hartley
*Assistant Examiner* — Jagadishwar Samala
(74) *Attorney, Agent, or Firm* — Nixon Peabody LLP

(57) ABSTRACT

The present invention teaches devices and methods for hyperpolarization by parahydrogen induced polarization. The invention teaches several significant improvements over previous designs, including a heating block, an enhanced solenoid component, and pinch valves and tubing that provide a sterile environment for the sample. All of these advancements can be accomplished while keeping costs to produce the device relatively low.

10 Claims, 27 Drawing Sheets

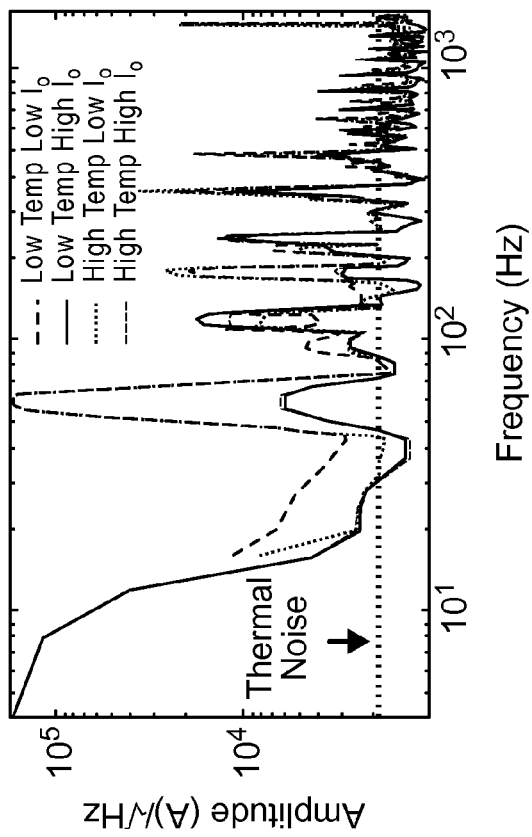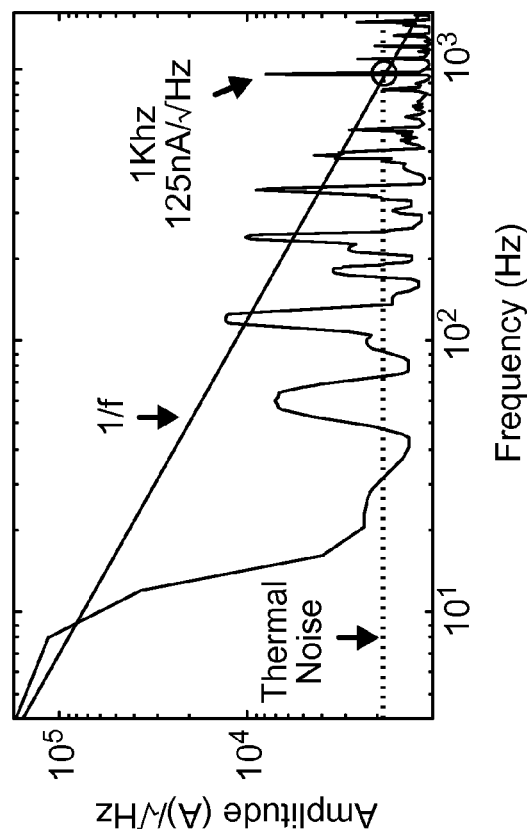
*Figure 19A*
*Figure 19B*

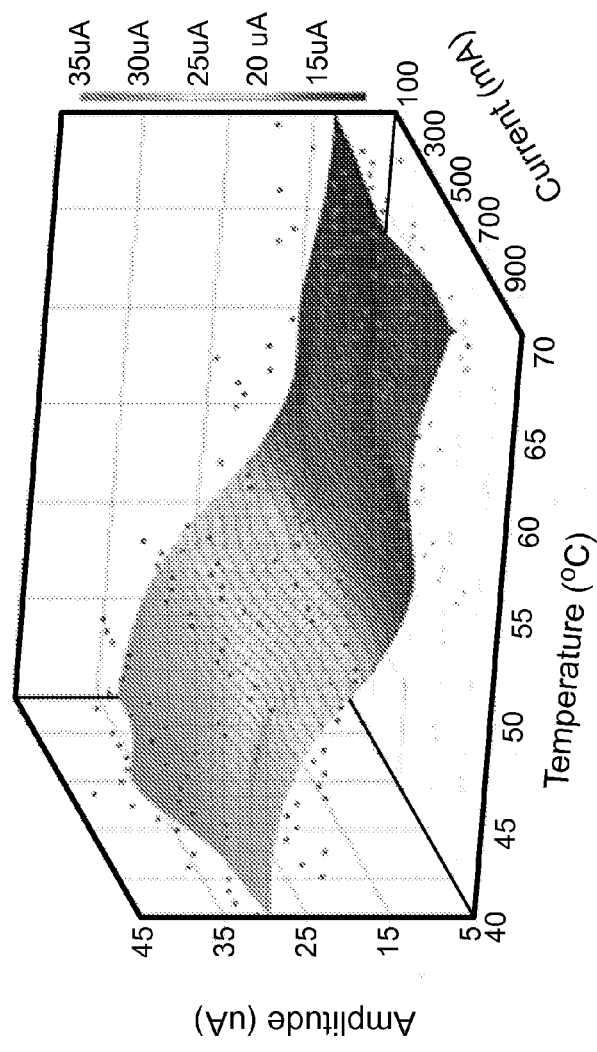
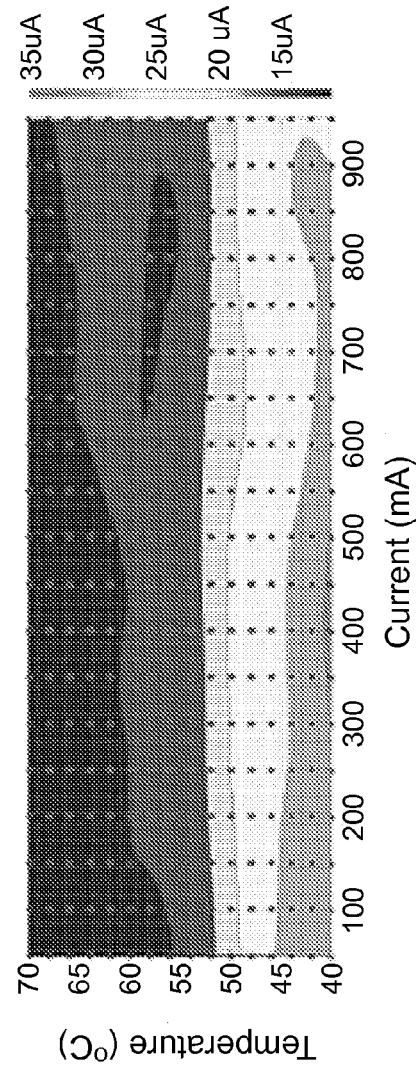
Figure 20A
Figure 20B

DEVICES AND METHODS FOR PARAHYDROGEN INDUCED POLARIZATION

CROSS-REFERENCE TO RELATED APPLICATIONS

This application is the National Phase of International Application PCT/US2013/058625, filed Sep. 6, 2013, which designated the U.S. and that International Application was published under PCT Article 21(2) in English. This application also claims priority under 35 U.S.C. 119(e) to U.S. Provisional Application No. 61/698,488 filed Sep. 7, 2012, which is hereby incorporated by reference in its entirety.

STATEMENT REGARDING FEDERALLY-SPONSORED RESEARCH

This invention was made with government support under W81XWH-11-1-0169 awarded by the Department of Defense. The government has certain rights in the invention.

FIELD OF INVENTION

This invention generally relates to improvements in technology used to facilitate hyperpolarization by parahydrogen induced polarization.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Hyperpolarization is emerging as a technology for probing metabolic processes in vivo. In the field of parahydrogen induced polarization (PHIP), equipment is only available through construction by individual researchers. Impediments to more widespread use of hyperpolarization, and its use in in vivo human studies, include difficulties with uniformly controlled sample heating and sterility, and the need for more reliable and effective software to run the components of the hyperpolarization device. Thus, there is a need in the art for improved devices and methods for facilitating hyperpolarization by parahydrogen induced polarization.

SUMMARY OF THE INVENTION

In various embodiments, the invention teaches a device for parahydrogen induced polarization, including: (1) a reactor, including a first reactor inlet, a second reactor inlet, and a reactor outlet; (2) a precursor receiving tube, including a first precursor receiving tube end and a second precursor receiving tube end, wherein the first precursor receiving tube end is mechanically connected to the first reactor inlet; (3) a parahydrogen receiving tube, including a first parahydrogen receiving tube end and a second parahydrogen receiving tube end, wherein the first parahydrogen receiving tube end is mechanically connected to the second reactor inlet; (4) an outlet tube, including a first outlet tube end and a second outlet tube end, wherein the first outlet tube end is mechanically connected to the reactor outlet; (5) a radio frequency (RF) coil enveloping the reactor along the vertical axis thereof; (6) a solenoid coil enveloping the RF coil along the vertical axis thereof; and (7) a metal heating block, including a longitudinal axis that includes a plurality of grooves situated perpendicular thereto, wherein each of the plurality of grooves are configured to accommodate a section of the precursor receiving tube, and wherein the section of the precursor receiving tube is wrapped around the grooves of the metal heating block. In some embodiments, the device includes one or more pinch valves, wherein the pinch valves are configured to compress one or more segments of one or more of the precursor receiving tube, the parahydrogen receiving tube and the outlet tube.

In various embodiments, the invention teaches a device for parahydrogen induced polarization, including: (1) a reactor, including a first reactor inlet, a second reactor inlet, and a reactor outlet; (2) a precursor receiving tube, including a first precursor receiving tube end and a second precursor receiving tube end, wherein the first precursor receiving tube end is mechanically connected to the first reactor inlet; (3) a parahydrogen receiving tube, including a first parahydrogen receiving tube end and a second parahydrogen receiving tube end, wherein the first parahydrogen receiving tube end is mechanically connected to the second reactor inlet; (4) an outlet tube, including a first outlet tube end and a second outlet tube end, wherein the first outlet tube end is mechanically connected to the reactor outlet; (5) a radio frequency (RF) coil enveloping the reactor along the vertical axis thereof; (6) a solenoid coil enveloping the RF coil along the vertical axis thereof; and (7) one or more pinch valves, wherein the pinch valves are configured to compress one or more segments of one or more of the precursor receiving tube, the parahydrogen receiving tube and the outlet tube.

In some embodiments, the device further includes a metal heating block including a longitudinal axis that includes a plurality of grooves situated perpendicular thereto, wherein each of the plurality of grooves are configured to accommodate a section of the precursor receiving tube, and wherein the section of the precursor receiving tube is wrapped around the grooves of the metal heating block.

In some embodiments the devices described herein also include a wire for applying an electrical current to the RF coil. In some embodiments, the devices include a wire for applying an electrical current to the solenoid coil. In certain embodiments, the devices include a circuit connected to the solenoid coil, wherein the circuit is configured to control the current in the solenoid coil. In various embodiments, the circuit is configured to maintain the current at 0.770+/−0.002 A. In various embodiments, the solenoid further includes end-ring loops and mid-ring loops made of wire, and wherein the wire is configured to increase center field homogeneity compared to a solenoid without the end-ring loops and the mid-ring loops. In some embodiments, the metal heating block is aluminum. In various embodiments, a fan is situated below the metal heating block, and the fan is configured to equilibrate the metal heating block at a temperature of 60° C. in 30 minutes during the initial start-up of the device for parahydrogen induced polarization. In various embodiments, the reactor is made of polysulfone. In certain embodiments, one or more of the precursor receiving tube, parahydrogen receiving tube and outlet tubes is a silicone tube surrounded by a more rigid plastic tube. In various embodiments, one or more of the precursor receiving tube, parahydrogen receiving tube and outlet tubes is made of silicone and polytetrafluoroethylene (PTFE). In certain embodiments, one or more of the pinch valves are functional at a pressure of up to 100 pounds per square inch. In certain embodiments, the pinch valves are electronically controlled by activation input. In certain embodiments, the activation input of the pinch valves is 15V when the valve is closed. In certain embodiments, the voltage is automatically reduced to 5V when the valve is open. In some embodiments, the device further includes electronic components for controlling one or more of (1) one or more of the valves of the device, (2) the solenoid coil and (3) the RF coil. In certain embodiments, the operation of the electronic components is controlled by software. In various embodiments, the software is configured with instructions for the device to generate an RF transfer pulse sequence with excitation at a first bandwidth corresponding to a hydrogen nuclei and a second bandwidth corresponding to a hyperpolarizable nuclei, when the instructions are executed. In certain embodiments, the hyperpolarizable nuclei is $^{13}C$ or $^{15}N$. In some embodiments, the software includes instructions for the device to generate the RF transfer pulse sequence based on three required scalar coupling constants, including $J_{1H-2H}$, $J_{1H-X}$ and $J_{2H-X}$, wherein X is a hyperpolarizable nuclei.

In various embodiments, the invention teaches a method, including: (1) providing a device, including: (a) a reactor, including a first reactor inlet, a second reactor inlet, and a reactor outlet; (b) a precursor receiving tube, including a first precursor receiving tube end and a second precursor receiving tube end, wherein the first precursor receiving tube end is mechanically connected to the first reactor inlet; (c) a parahydrogen receiving tube, including a first parahydrogen receiving tube end and a second parahydrogen receiving tube end, wherein the first parahydrogen receiving tube end is mechanically connected to the second reactor inlet; (d) an outlet tube, including a first outlet tube end and a second outlet tube end, wherein the first outlet tube end is mechanically connected to the reactor outlet; (e) a radio frequency (RF) coil enveloping the reactor along the vertical axis thereof; (f) a solenoid coil enveloping the RF coil along the vertical axis thereof; (g) a metal heating block including a longitudinal axis that contains a plurality of grooves situated perpendicular thereto, wherein each of the plurality of grooves are configured to accommodate a section of the precursor receiving tube, and wherein the section of the precursor receiving tube is wrapped around the grooves of the metal heating block; and (h) one or more pinch valves, wherein the pinch valves are configured to compress one or more segments of one or more of the precursor receiving tube, the parahydrogen receiving tube and the outlet tube; (2) introducing a quantity of parahydrogen into the reactor through the parahydrogen receiving tube; (3) introducing a sample including an imaging molecule precursor including a $^{13}C$ or $^{15}N$ nuclei into the precursor receiving tube; (4) heating the sample with the heating block; (5) advancing the heated sample into the reactor; (6) using the solenoid coil to establish a static magnetic field; (7) using the RF coil to apply an RF transfer pulse sequence with excitation at a first bandwidth corresponding to a hydrogen nuclei, and a second bandwidth corresponding to a hyperpolarizable nuclei of an imaging molecule, thereby generating a hyperpolarized imaging molecule; and (8) removing the hyperpolarized imaging molecule from the device. In some embodiments, the heating block heats the sample to 60° C. In some embodiments, the heated sample includes a catalyst. In some embodiments, the method also includes, (1) removing the catalyst; (2) injecting the hyperpolarized imaging molecule into a subject after the catalyst has been removed; and (3) imaging the subject using NMR imaging. In various embodiments, the hyperpolarized imaging molecule is implicated in metabolism. In certain embodiments, the invention teaches a hyperpolarized imaging molecule produced by performing any of the methods described herein.

BRIEF DESCRIPTION OF THE DRAWINGS

Exemplary embodiments are illustrated in the referenced figures. It is intended that the embodiments and figures disclosed herein are to be considered illustrative rather than restrictive.

FIG. 19 depicts, in accordance with an embodiment of the invention, a VCCS noise spectrum measured using the Agilent 35670A. a) Noise at the four corners (extremes). b) Average noise.

FIG. 20 depicts, in accordance with an embodiment of the invention, VCCS noise amplitude measured using the Agilent 35670A. a) Three-dimensional plot. b) Countour plot.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. March, *Advanced Organic Chemistry Reactions, Mechanisms and Structure* $5^{th}$ *ed.* provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Mammal" as used herein refers to a member of the class Mammalia, including, without limitation, humans as well as nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, newborn subjects and infant subjects, as well as fetuses, whether male or female, are intended to be included within the scope of this term.

In some embodiments, the numbers expressing quantities of ingredients, properties such reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Advantages and Applications of Hyperpolarization

Figure 22A:
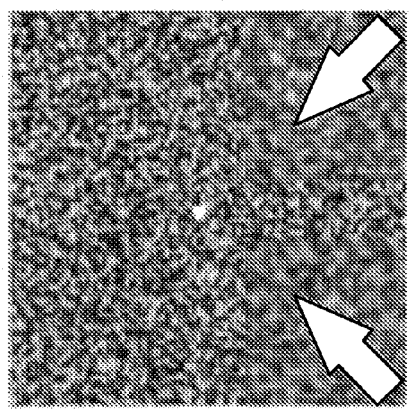
FIG. 22 depicts, in accordance with an embodiment of the invention, a hyperpolarized $^{13}C$ molecule vs. normal $^{13}C$ molecule signal. a) $^{13}C$ molecule signal at equilibrium, b) Resulting MRI image, c) Hyperpolarized $^{13}C$ molecule, 10,000 times more signal amplitude, d) Resulting MRI image.
Figure 22B:
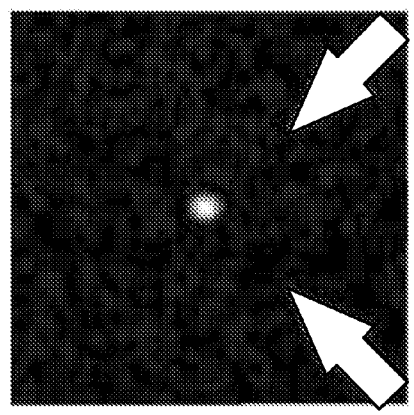
Figure 22C:
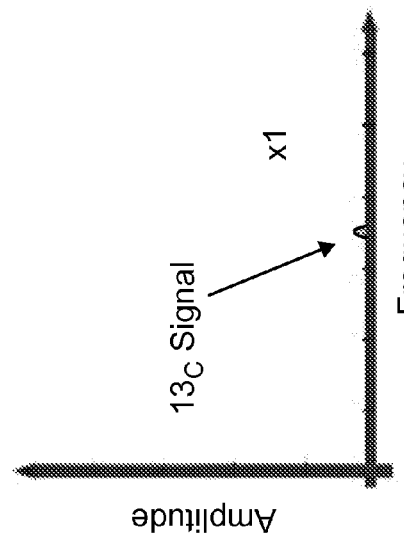
Figure 22D:
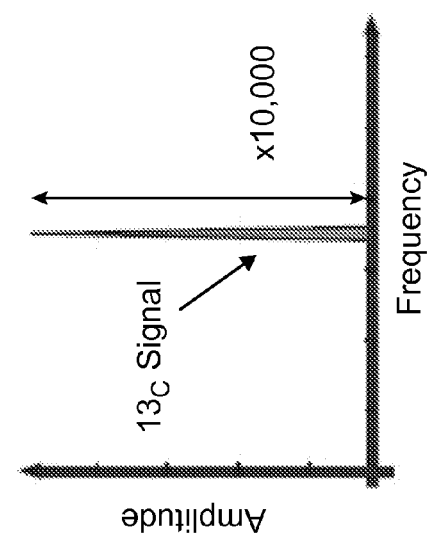

By way of background, cancer, Alzheimer's disease, heart disease, and stroke are the leading causes of death and debilitation among Americans. These illnesses are poorly diagnosed at early stages and linked with high morbidity and mortality. The current gold standard for screening cardiac muscle ischemia, cancer, and Alzheimer's disease varies from a simple self-exam (breast cancer), blood levels of troponin test (heart ischemia), computerized tomography (CT) scan (ischemia, cancer, Alzheimer's disease), and invasive needle and excisional biopsies. However, due to these methods' inherent insensitivity to signal detection, they are inadequate for early disease diagnosis (FIGS. 22a & 22b). Advantageously, hyperpolarizing metabolites using the PHIP method allows for MRI signals to increase in amplitude from 30,000 to 100,000 fold (FIGS. 22c and 22d). Furthermore, using hyperpolarized metabolites, images are generated by viewing the hyperpolarized nuclei directly. The greater the concentration of hyperpolarized nuclei the larger the signal.

The PHIP Method

Figure 23A:
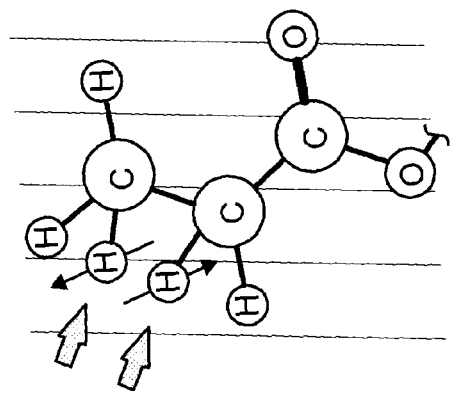
FIG. 23 depicts, in accordance with an embodiment of the invention, hyperpolarization of a molecule from a precursor molecule with a double bond, light gray lines signify the main magnetic field $B_o$. a) Double bond weakening by Catalyst, b) Precursor hydrogenation with para-Hydrogen, c) Spin transfer by RF irradiation, d) Spin transferred to $^{13}C$ atom.
Figure 23B:
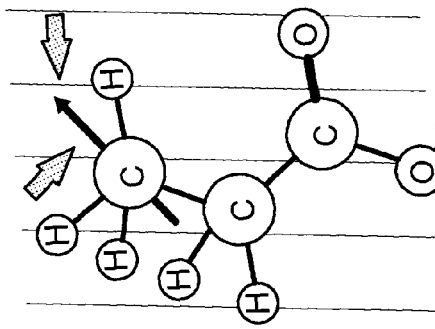
Figure 23C:
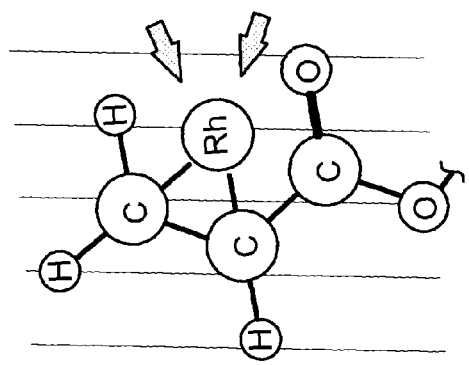
Figure 23D:
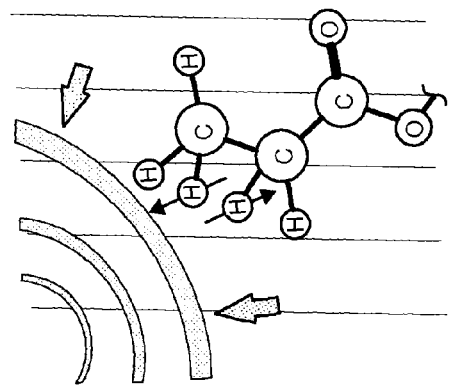

The PHIP method is based on the chemical addition of parahydrogen (para-$H_2$) to a substrate or precursor molecule (gas or liquid). This precursor is prepared with a Rhodium (Rh) catalyst complex that weakens the 13-Carbon ($^{13}C$) double bond (FIG. 23a). The mixing of para-$H_2$ and the precursor occurs in a reaction chamber, where a Rh catalyst assists a hydrogenation reaction, adding two para-$H_2$ atoms across the carbon-carbon double bond (FIG. 23b). Then, the Rh complex dislodges. By irradiating the mix with radio frequency (RF) pulses (FIG. 23c), the spin energy transfers from the added hydrogen atoms to $^{13}C$ in the newly created molecule. This method results in a signal enhancement of 30,000 or more (FIGS. 22c, 22d, & 23d).

Unfortunately, in the field of PHIP, equipment is only available through construction by individual researchers. As described in detail below, the inventors have improved upon published designs, such as those described in Hovener J B, et. al. MAGMA 2009; 22(2): 111-21 (hereafter referred to as Hovener); and Waddell K W, et al. JACS 2011; 133:97-101 (hereafter referred to as Waddell), and have updated the operational software to improve reliability and assist in the functional operation. More specifically, in certain embodiments described herein, the new design incorporates a controlled sample heating block and a sealed sample preparation system that can be easily removed for sterilization. Further, as PHIP requires an RF transfer pulse sequence with excitation at two bandwidths corresponding to the hydrogen nuclei and hyperpolarizable nuclei (X nuclei), the inventors developed software that generates the required transfer pulse sequence based on the three required scalar coupling constants $J_{1H-2H}$, $J_{1H-X}$ and $J_{2H-X}$. In some embodiments, the device described herein maintains a 1.8 mT static magnetic field, allowing for use of commercially available low cost amplifiers. Advantageously, the parts cost for building the polarizer is relatively low, with minimal operating costs. In fact, PHIP using the inventive devices and methods is almost two orders of magnitude cheaper than competing commercial dynamic nuclear polarization (DNP) equipment requiring continual helium replacement. Further, the hydrogenation reaction utilizing the inventive device can be carried out in 2 seconds, with 100% yield.

Importantly, although numerous configurations of the inventive components and devices are described herein below, one of skill in the art would readily appreciate that each of the inventive components could be used to modify and improve a number of hyperpolarization devices, including, but in no way limited to those described in Hovener and Waddell. For example, the tubing and pinch valves described herein could be used to substitute for the tubing and valves described in each of the aforementioned references. Similarly, the devices described in Hovenor and Waddell, and other devices used for hyperpolarization, could be modified to include the solenoid and/or circuit design and/or heating components taught by the present invention. Furthermore, the software described herein could be modified to facilitate PHIP in alternative devices, in addition to those described herein.

In various embodiments, the invention teaches a device for parahydrogen induced polarization, including: (1) a reactor with a superior reactor side and an inferior reactor side, wherein the superior reactor side includes a first reactor inlet and a second reactor inlet, and the inferior reactor side includes a reactor outlet; (2) a precursor receiving tube, including a first precursor receiving tube end and a second precursor receiving tube end, wherein the first precursor receiving tube end is mechanically connected to the first reactor inlet; (3) a parahydrogen receiving tube, including a first parahydrogen receiving tube end and a second parahydrogen receiving tube end, wherein the first parahydrogen receiving tube end is mechanically connected to the second reactor inlet; (4) an outlet tube, including a first outlet tube end and a second outlet tube end, wherein the first outlet tube end is mechanically connected to the reactor outlet; (5) a radio frequency (RF) coil enveloping the reactor along the vertical axis thereof; (6) a solenoid coil enveloping the RF coil along the vertical axis thereof; and (7) a metal heating block with a longitudinal axis including a plurality of grooves situated perpendicular thereto, wherein each of the plurality of grooves are configured to accommodate a section of the precursor receiving tube, and wherein the section of the precursor receiving tube is wrapped around the grooves of the metal heating block. In some embodiments, the device includes one or more pinch valves, wherein the pinch valves are configured to compress one or more segments of one or more of the precursor receiving tube, the parahydrogen receiving tube, and the outlet tube.

In various embodiments, the invention teaches a device for parahydrogen induced polarization, including: (1) a reactor with a superior reactor side and an inferior reactor side, wherein the superior reactor side includes a first reactor inlet and a second reactor inlet, and the inferior reactor side includes a reactor outlet; (2) a precursor receiving tube, including a first precursor receiving tube end and a second precursor receiving tube end, wherein the first precursor receiving tube end is mechanically connected to the first reactor inlet; (3) a parahydrogen receiving tube, including a first parahydrogen receiving tube end and a second parahydrogen receiving tube end, wherein the first parahydrogen receiving tube end is mechanically connected to the second reactor inlet; (4) an outlet tube, including a first outlet tube end and a second outlet tube end, wherein the first outlet tube end is mechanically connected to the reactor outlet; (5) a radio frequency (RF) coil enveloping the reactor along the vertical axis thereof; (6) a solenoid coil enveloping the RF coil along the vertical axis thereof; and (7) one or more pinch valves, wherein the pinch valves are configured to compress one or more segments of one or more of the precursor receiving tube, the parahydrogen receiving tube and the outlet tube. In some embodiments, the device includes a metal heating block with a longitudinal axis that includes a plurality of grooves situated perpendicular thereto, wherein each of the plurality of grooves are configured to accommodate a section of the precursor receiving tube, and wherein the section of the precursor receiving tube is wrapped around the grooves of the metal heating block. In some embodiments, the metal heating block described herein is cylindrical. In some embodiments, the reactor described herein is cylindrical.

In some embodiments, the devices described herein include a wire for applying an electrical current to the RF coil. In some embodiments, the devices described herein include a wire for applying an electrical current to the solenoid coil. In some embodiments, the devices described herein include a circuit connected to the solenoid coil, wherein the circuit is configured to control the current in the solenoid coil. In some embodiments, the circuit is configured to maintain the current at 0.770+/−0.002 A. In some embodiments, the current is maintained between 700 ma and 800 ma. In some embodiments, the solenoid further includes end-ring loops and mid-ring loops made of wire, and the wire is configured to increase center field homogeneity compared to a solenoid without the end-ring loops and the mid-ring loops. In some embodiments, the heating block can be made of any metal into which hose grooves can be machined. In certain embodiments, the heating block of the devices described herein is made of aluminum. In some embodiments, the heating block is solid. In some embodiments, the device includes a fan situated below the heating block, and the fan is configured to equilibrate the heating block at a temperature of between 30° C. and 80° C. In some embodiments, the rate is dynamic and controlled by a heater controller (such as one produced by Omega Engineering). In some embodiments, the fan is configured to equilibrate the heating block at a temperature of 60° C. in 30 minutes during the initial start-up of the device for parahydrogen induced polarization. In certain embodiments, the reaction chamber is made of polysulfone. One of skill in the art would readily appreciate that materials with similar characteristics to polysulfone could also be used in conjunction with the inventive devices and methods described herein. In preferred embodiments, the material used for the reaction chamber is transparent to RF. In certain embodiments, one or more of the precursor receiving tube, parahydrogen receiving tube and outlet tubes include a silicone tube surrounded by a more rigid plastic tube. In alternative embodiments, one or more of the tubes can be made of a material with characteristics similar to silicon. In some embodiments, one or more of the tubes includes silicone and polytetrafluoroethylene (PTFE). In some embodiments, one or more of the pinch valves are functional at a pressure of between 0 to 100 pounds per square inch. In some embodiments, one or more of the pinch valves are functional at a pressure of between 0 to 90 pounds per square inch. In some embodiments, one or more of the pinch valves are functional at a pressure of between 0 to 50 pounds per square inch. In some embodiments, one or more of the pinch valves are functional at a pressure up to 100 pounds per square inch. In certain embodiments, the pinch valves are electronically controlled by activation input. In some embodiments, the pinch valve is controlled by a step function. The first is 24 v, while the hold state is 4 v. In some embodiments, the valve's power off state is closed and the valve opens when activated. In some embodiments, the power is reduced from 24 v to 4 v. In some embodiments, the activation input of the pinch valves is 15V when the valve is closed. In certain embodiments, the voltage is automatically reduced to 5V when the valve is open. One of skill in the art would readily appreciate that these parameters could be changed to different values, so long as similar results are achieved. In some embodiments, the device includes electronic components for controlling one or more of (1) one or more of the valves of the system, (2) the solenoid coil and (3) the RF coil. In certain embodiments, the operation of the electronic components is controlled by software. In some embodiments, the software is embodied in a non-transitory computer readable medium executable by a processor. Greater detail regarding the operation and configuration of the software is provided herein below in the Examples section. In certain embodiments, the software is configured with instructions for a device described herein to generate an RF transfer pulse sequence with excitation at a first bandwidth corresponding to a hydrogen nuclei and a second bandwidth corresponding to a hyperpolarizable nuclei, when the instructions are executed. In certain embodiments, the hyperpolarizable nuclei is $^{13}C$ or $^{15}N$. In some embodiments, the software includes instructions for the device to generate the RF transfer pulse sequence based on three required scalar coupling constants, including $J_{1H-2H}$, $J_{1H-X}$ and $J_{2H-X}$, wherein X is a hyperpolarizable nuclei.

In various embodiments, the invention teaches a method for using a hyperpolarizing device. In some embodiments, the device includes (a) a reactor with a superior reactor side and an inferior reactor side, wherein the superior reactor side includes a first reactor inlet and a second reactor inlet, and the inferior reactor side includes a reactor outlet; (b) a precursor receiving tube, including a first precursor receiving tube end and a second precursor receiving tube end, wherein the first precursor receiving tube end is mechanically connected to the first reactor inlet; (c) a parahydrogen receiving tube, including a first parahydrogen receiving tube end and a second parahydrogen receiving tube end, wherein the first parahydrogen receiving tube end is mechanically connected to the second reactor inlet; (d) an outlet tube, including a first outlet tube end and a second outlet tube end, wherein the first outlet tube end is mechanically connected to the reactor outlet; (e) a radio frequency (RF) coil enveloping the reactor along the vertical axis thereof; (f) a solenoid coil enveloping the RF coil along the vertical axis thereof; (g) a metal heating block with a longitudinal axis that includes a plurality of grooves situated perpendicular thereto, wherein each of the plurality of grooves are configured to accommodate a section of the precursor receiving tube, and wherein the section of the precursor receiving tube is wrapped around the grooves of the metal heating block; and (h) one or more pinch valves, wherein the pinch valves are configured to compress one or more segments of one or more of the precursor receiving tube, the parahydrogen receiving tube and the outlet tube. In some embodiments, the method includes: (1) introducing a quantity of parahydrogen into the reactor through the parahydrogen receiving tube; (2) introducing a sample including an imaging molecule precursor including a $^{13}C$ or $^{15}N$ nuclei into the precursor receiving tube; (3) heating the sample with the heating block; (4) advancing the heated sample into the reactor; (5) using the solenoid coil to establish a static magnetic field; (6)

using the RF coil to apply an RF transfer pulse sequence with excitation at a first bandwidth corresponding to a hydrogen nuclei, and a second bandwidth corresponding to a hyperpolarizable nuclei of an imaging molecule, thereby generating a hyperpolarized imaging molecule; and (7) removing the hyperpolarized imaging molecule from the device. In some embodiments, the heating block heats the sample to 60° C. One of skill in the art would readily appreciate that alternative temperatures could be used, including those temperatures described in the example section. In certain embodiments, the heated sample includes a catalyst. In some embodiments, the invention further includes (a) removing the catalyst from the hyperpolarized sample; (b) injecting the hyperpolarized imaging molecule into a subject after the catalyst has been removed; and (c) imaging the subject using NMR imaging.

In some embodiments, the imaging molecule, or its precursor, is implicated in metabolism. In some embodiments, the imaging molecule precursor can be any molecule with an hyperpolarizable nuclei. In various embodiments, the PHIP precursor is a molecule that has a double or triple Carbon 13 bond. In some embodiments, the imaging molecule precursor can include, but is no way limited to fumarate.

In certain embodiments, the method described herein is performed on a device configured without a heating block of the type described herein, but with one or more pinch valves, in which case the sample is heated by an alternative method known in the art. In some embodiments, the method is performed on a device with a heating block described herein, but without the pinch valves described herein, in which case fluid flow is regulated by alternative method known in the art.

Figure 3:
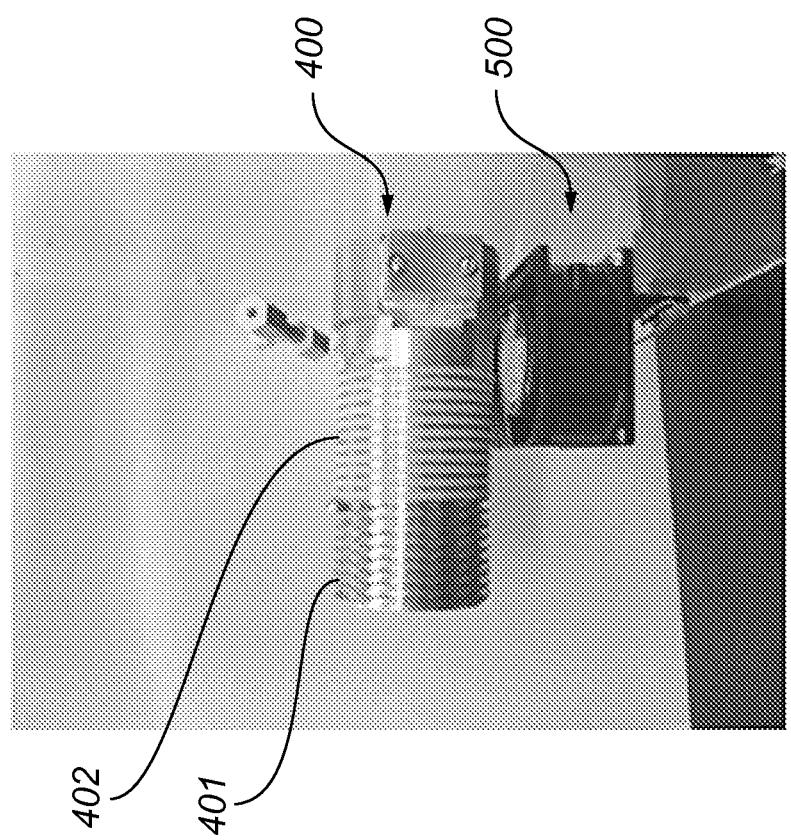
FIG. 3 depicts, in accordance with an embodiment of the invention, a solid aluminum cylinder with grooves machined to fit the polytetrafluoroethylene (PTFE) tubing carrying the sample. Heating occurs through conduction with the large mass of aluminum. A fan is positioned under the block to allow the block to equilibrate at the polarization temperature of 60° C. in 30 minutes through convection during the initial startup of the system.
Figure 4:
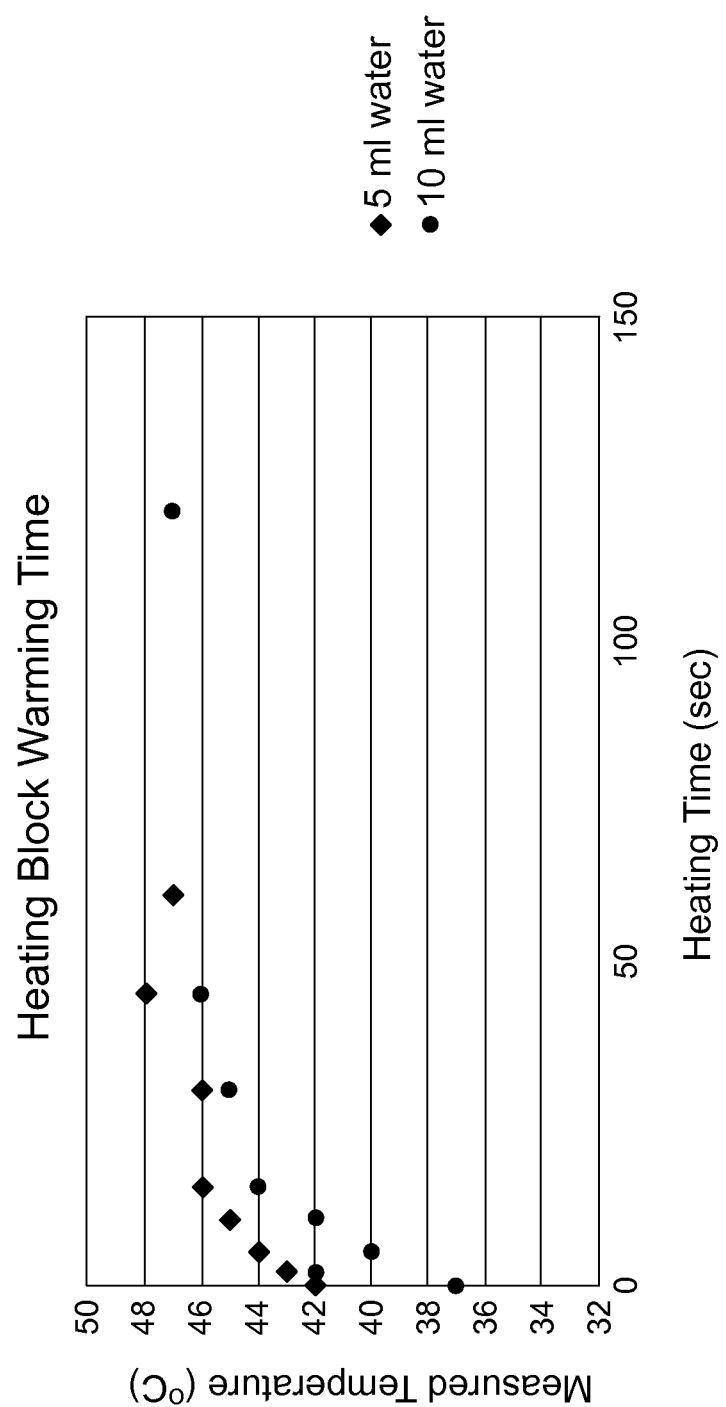
FIG. 4 depicts, in accordance with an embodiment of the invention, calibration curves showing the required heating time of the sample to achieve the set temperature. The heating block and internal temperature were 60° C. The temperature was measured with a thermocouple after ejection of the sample. The equilibration to the maximum recorded temperature indicates the required heating time. 5 mL of water required about 50 seconds, and 10 mL of water required about 60 seconds.
Figure 5:
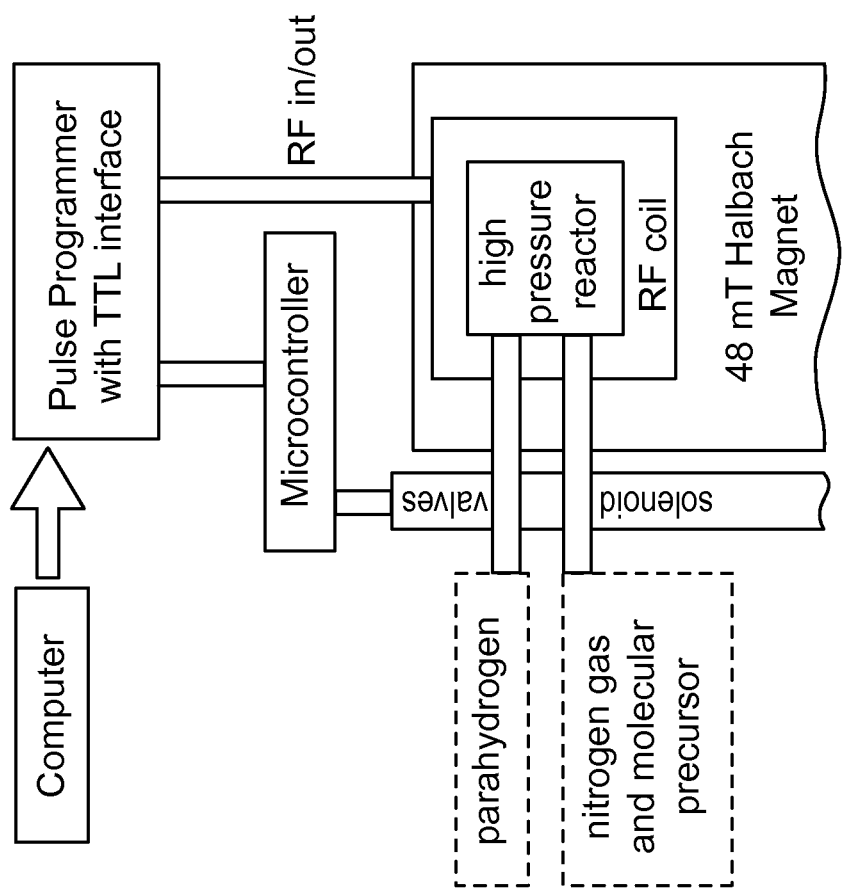
FIG. 5 depicts, in accordance with an embodiment of the invention, a diagram of a system for hyperpolarization described in Waddell K W, et al. JACS 2011; 133:97-101.
Figure 6:
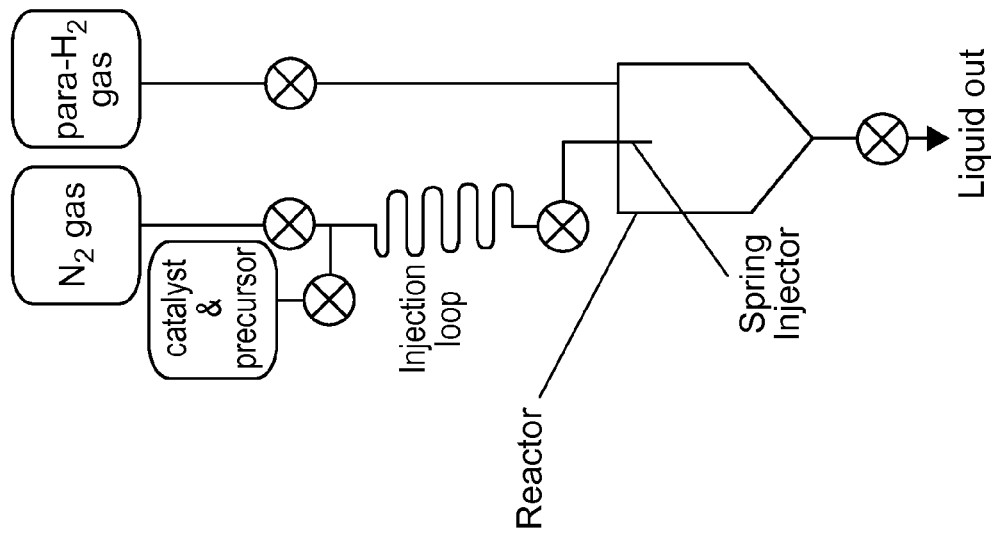
FIG. 6 depicts, in accordance with an embodiment of the invention, an image and a diagram of a system for hyperpolarization described in Waddell K W, et al. JACS 2011; 133:97-101.
Figure 7:
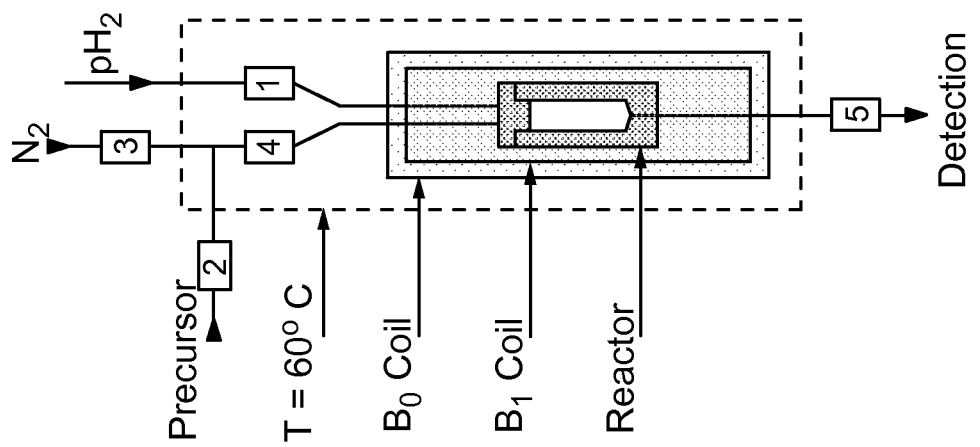
FIG. 7 depicts, in accordance with an embodiment of the invention, a diagram of a system described in Hovener J B, et. Al. MAGMA 2009; 22(2): 111-21.

In some embodiments, the invention teaches a metal heating cylinder 400, such as the one depicted in FIG. 3. In some embodiments, the metal heating cylinder 400 is configured with or connected to a mechanism that generates heat. In some embodiments, the metal heating cylinder 400 includes a longitudinal axis including a plurality of grooves 401 situated perpendicular thereto, wherein each of the plurality of grooves 401 are configured to accommodate a section of tubing 402.

In some embodiments, the invention teaches a system for regulating the temperature of a sample within a tube. In certain embodiments, the system includes a metal heating cylinder 400 with a plurality of grooves 401 as described above, and a fan 500 situated in close proximity to the metal heating cylinder, as depicted in FIG. 3.

EXAMPLES

Example 1

Overview of Advancements

This section provides a general overview of certain improvements to PHIP devices and methods developed by the inventors. More detailed descriptions of some aspects of these improvements are included in subsequent examples.

Solenoid Coil

One of the major design difficulties with PHIP at low field is determining the static magnet field, $B_0$, and calibrating the pulses. Typically the RF pulses are calibrated by equilibrating a sample in a spectrometer, quickly transferring the sample to the polarizer and delivering an RF pulse. The sample is then returned to the spectrometer and a read pulse is used to determine the Z magnetization. When the system is closed and heated, the resistance in the copper coil increases. Maintaining the static magnetic field requires a greater voltage potential to drive the same current. Therefore, the inventors have implemented a circuit that controls the current at 0.770+/−0.002 A. Extra end ring loops have also been added to the solenoid magnetic field coil to increase the center field homogeneity, which minimizes signal loss due to unrecoverable spin-spin dephasing. Through the approach described herein, the inventors have reduced dephasing errors to increase the maximum polarization potential.

Figure 1B:
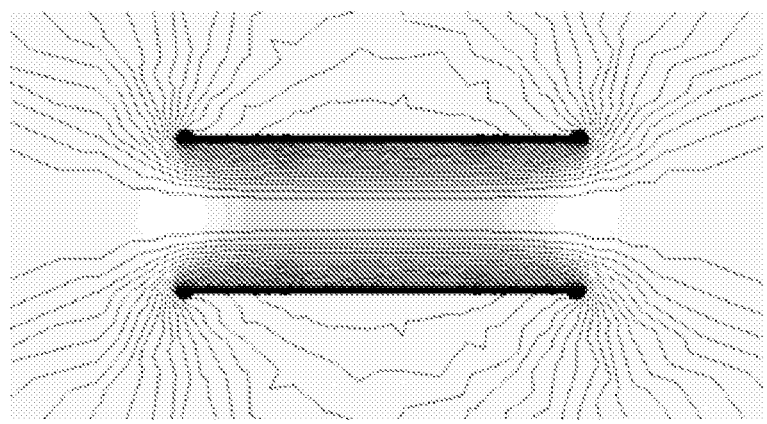
FIG. 1B depicts a finite element modeled magnetic (FEMM) field. End-rings and mid-rings were added to increase the middle two centimeters of the coils field homogeneity empirically. The field homogeneity in the center two centimeters is calculated at 1000 ppm (0.1%).
Figure 1A:
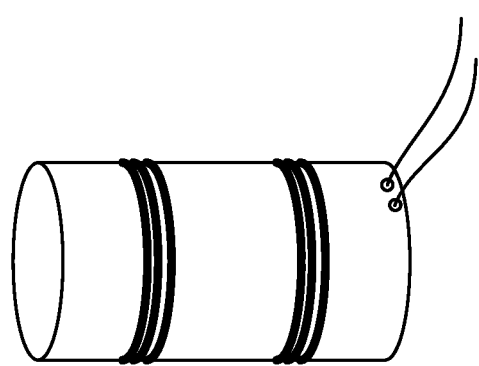
FIG. 1A depicts, in accordance with an embodiment of the invention, a solenoid wrapped with 20 gauge wire.
Figure 2:
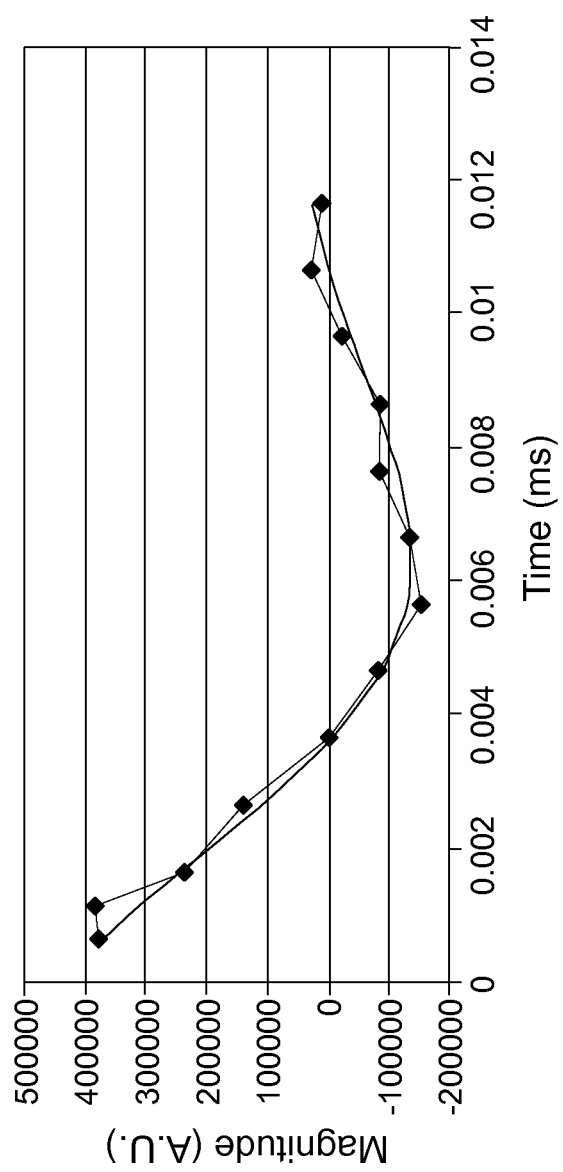
FIG. 2 depicts, in accordance with an embodiment of the invention, a graph demonstrating free induction decay generated by polarizing a 0.5 g solution of $^{15}N$-choline in a 9.4 T magnetic field for 3 minutes, transferring the sample to the 1.8 mT field, delivering a 90-x degree pulse, waiting time, t, returning the magnetization to the Z-axis with a 90-x pulse, and then measuring the remaining magnetization in the 9.4 T field. The black line is the fit with a 70 Hz off resonance, and a decay constant of 6 ms. The diamonds are the acquired data points.

To assess the coil quality and determine the resonance frequency, the inventors recorded the free inductance decay (FID) to determine the off resonance shift. The FID when fit to an exponential decay had a constant of T2*=6 ms; $M_O = M_\infty * exp(-t/T2*)$ (FIG. 2).

Sample Heating

PHIP while limited to a subset of molecules which have precursors with carbon double or triple bonds has both research and clinical potential to prepare biomarkers rapidly, on site, and without ionizing radiation. The fast sample preparation time of less than 2 minutes, can accelerate large group size studies and allow multiple dose experiments. PHIP has the potential to fill a niche with metabolic hyperpolarized 13C and 15N imaging, as indicated above.

Figure 15:
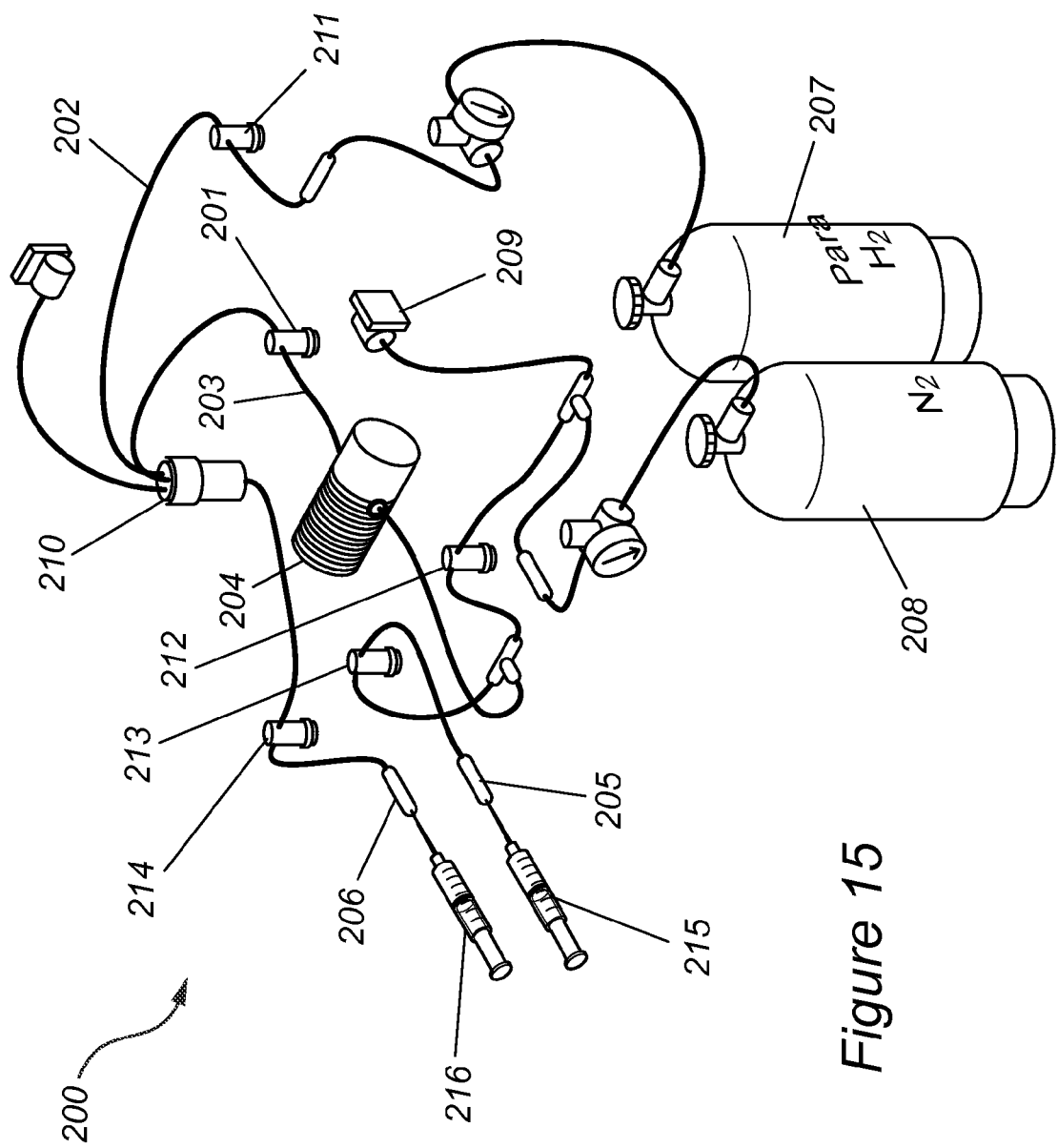
FIG. 15 depicts, in accordance with an embodiment of the invention, a PHIP Instrument displaying the basic components for hyperpolarization automation. The precursor sample was introduced into the system using a syringe. Next, the sample is moved to the heater block where the temperature is risen by conduction to 45° C. p-$H_2$ gas fills the chamber and $N_2$ pushes the sample in, where the precursor is hydrogenated. Finally, the sample is irradiated with RF, the spin transferred, and the polarized sample ejected.

As shown in FIGS. 3 and 15, a solid aluminum cylinder (with grooves machined to fit the PTFE tubing carrying the sample) can be used to heat the sample. Heating occurs through conduction with the large mass of aluminum. A fan is positioned under the block to allow the block to equilibrate at the polarization temperate of 60° C. in 30 minutes, through convection during the initial startup of the system described herein.

Sealed Valve System

For in vivo uses, the designs described herein allow for sterilization of all of the components. Specifically, the inventors have selected materials which can be replaced cheaply, or sterilized. The reaction chamber used in the inventive device can be made of polysulfone, and the sample transfer lines can be made of silicone and PTFE. The inventors have modified pinch valves rated at 25 PSI to be functional at pressures up to 100 PSI, by increasing the spring tension and replacing the standard silicone tubing with a silicone tube in a more rigid plastic tube. To accommodate the increased spring tension the inventors increased the activation input voltage from 12V to 15V. Once the valve is open, the voltage is dropped to 5V to prevent overheating of the valve. By using pinch valves the design prevents contact of the valve parts with the sample.

Results & Conclusions

The inventors have effectively produced a homogeneous magnetic field as demonstrated with a T2* of 6 ms for $^{15}N$ choline. Well shimmed line width in a 9.4 T system is 25 Hz (12 ms T2*). Sample heating can be accomplished in 1 minute, minimizing any catalyst decomposition and allowing for rapid sample production which is very useful for probing the metabolism of cells in vitro. Furthermore, the non-contact valves described above (and in greater detail below) can be utilized for sample control to produce the sterile system that would be required for in vivo clinical research.

The following additional detailed examples contain a number of equations. Each set of equations within each example is ordered sequentially beginning with the number one.

Example 2

PHIP Instrumentation Pinch Valve Design for Sample Delivery, Process, & Collection Introduction As indicated above, an important step towards the understanding of the hyperpolarization of endogenous substances is the study of sample management and sterility. Residue from previous hyperpolarized substances is often observed in parahydrogen induced polarization (PHIP) instrumentation hosing and solenoid valves, this residue affects the distribution and concentration of subsequent samples. The residue is often so extreme that precipitate forms in the reaction capsule clogging the hosing and coating the inside hoses with dark residue. This in turn may affect the PHIP instrument performance and sample polarization intensity.

Pinch valves control the flow of gas or liquid by constricting a flexible tube 600 using a plunger 304 driven by a solenoid 305 (FIG. 9), have no direct contact with fluids or gases, close around suspended particles, and are inexpensive. The first inexpensive dual hose pinch valve design with as few as 26 parts was developed in the early 1980's and was used for controlling chemical, bacteriological, medical or industrial processes, of liquid or gases. However, these devices were manufactured from metallic parts and were complicated to build and expensive, leading to modern pinch valves made of molded plastic with optimized power consumption to stroke ratio for maximum efficiency.

Current PHIP instruments use electromagnetic solenoid valves (ESV) with fixed hosing for sample control. However, fixed hosing inhibits a sterile environment and flow control optimization is non-existent. Furthermore, ESVs are also susceptible to stray magnetic fields and in some cases overheating. As demonstrated herein, the inventors modified an off-the-shelf pinch valve (Palmer-Cole, USA) in order to perform at higher pressures. As demonstrated herein, the inventors also designed an electronic circuit valve driver to incorporate with the pinch valve modifications. This driver improves flow control in valve open conditions by sequentially overdriving and underdriving the valve's solenoid. These two inventive features increase the valve's pressure capacity and minimize $B_o$ interference by stray magnetic field & overheating.

In addition to circuit valve driver theoretical & numerical simulations, and pinch valve modifications, the inventors present magnetic field and solenoid armature temperature measurements. The circuit models described herein are based on transfer functions (TF), which supply the basis for finding the circuit response characteristics without solving differential equations. First, using Matlab (Mathworks, USA) simulations the inventors developed their valve driver design's TF, which is estimated using the method of open-circuit time constants, followed by the system's output current/input voltage $$\left(\frac{I_o}{V_{in}}\right) TF.$$

Methods

The PHIP method for research and clinical purposes requires a sterile hosing where samples can be hyperpolarized and delivered to the target. A pinch valve with disposable tubing provides the sterile environment for hyperpolarization research. The inventors modified a mechanically pinched, open frame, electric, with a fail closed, pinch valve (FIG. 9), and designed an electronic circuit to drive this pinch valve (FIG. 10).

Pinch Valve

This type of Pinch valve is the most cost effective as production is simple in comparison to ESV valves, but has the lowest pressure rating. There are three basic components to the inventive pinch valve; the body, hose, and plunger. The valve body contains the solenoid and plunger that compresses the flexible hosing to open or close the flow. The hose contains the flow media that isolates the flow from the environment and contamination. Merely by way of non-limiting examples, hoses are often made of variety of rubber-like elastomers, such as buna-N, butyl, neoprene, nordel, hypalon, viton, silicone, polyurethane, polypropylene, white butyl, and odorless and tasteless white neoprene. The plunger can be a spring driven rounded tip bronze rod that keeps the hose pinched, in order to stop any flow through the hose. However, one of skill in the art would readily appreciate that alternative materials could also be used with similar results.

Figure 8:
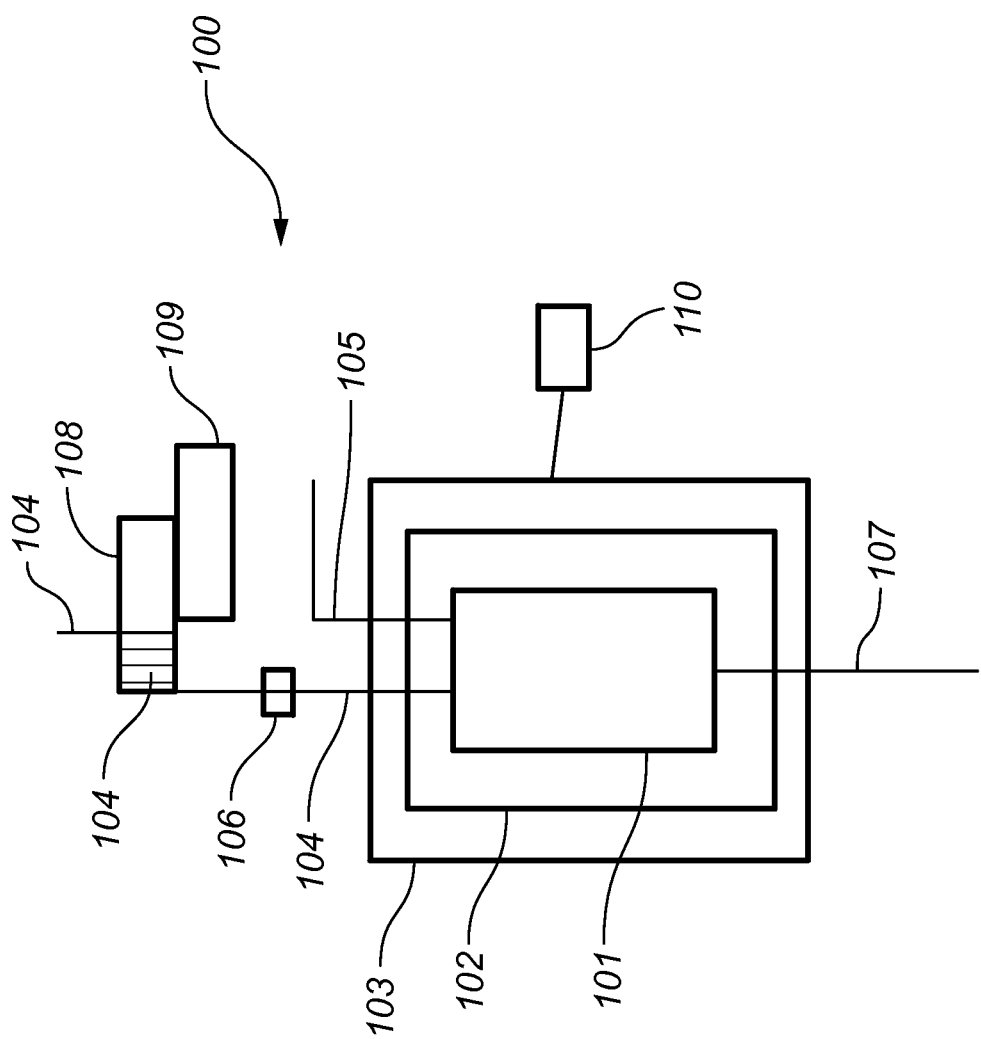
FIG. 8 depicts, in accordance with an embodiment of the invention, a diagram showing a device 100 for hyperpolarization, including a reactor 101; an RF coil 102; a solenoid 103; a first tube 104 connected to a first inlet of the reactor 101; a second tube 105 connected to a second inlet of the reactor 101; a pinch valve 106 for pinching the first tube 104, in order to regulate fluid flow; a third tube 107 connected to the outlet of the reactor 101; a heating block 108 around which a section of the first tube 104 is wrapped; a fan 109 for maintaining the temperature of the heating block 108; a circuit 110 for controlling the current in the solenoid 103.
Figure 9:
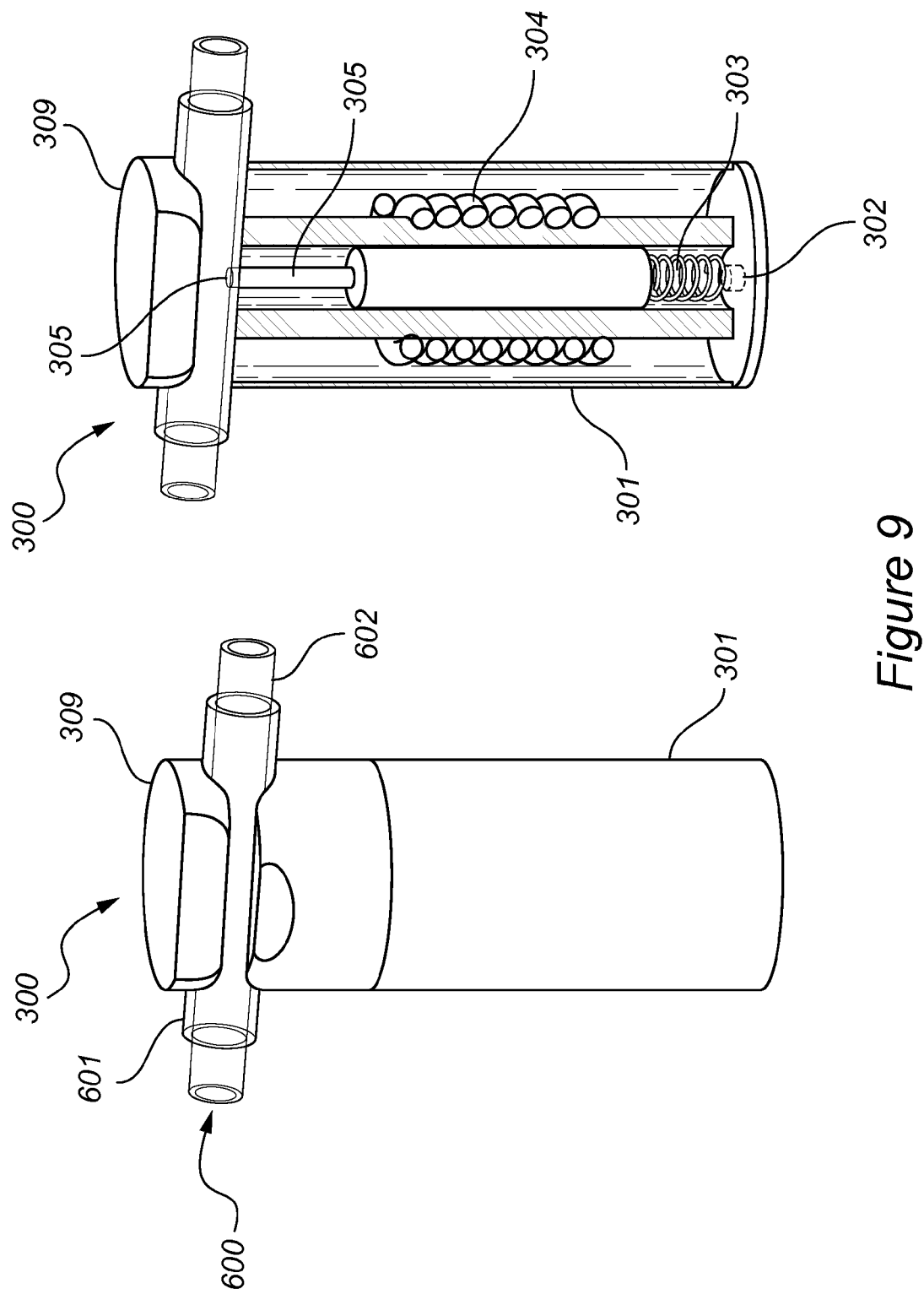
FIG. 9 depicts, in accordance with an embodiment of the invention, a modified pinch valve. The pressure rating was increased by placing a plastic sleeve around the silicon tubing at the pinch section. The pinch force spring was adjusted to the maximum in order keep the hose completely pinched and stop flow.
Figure 10:
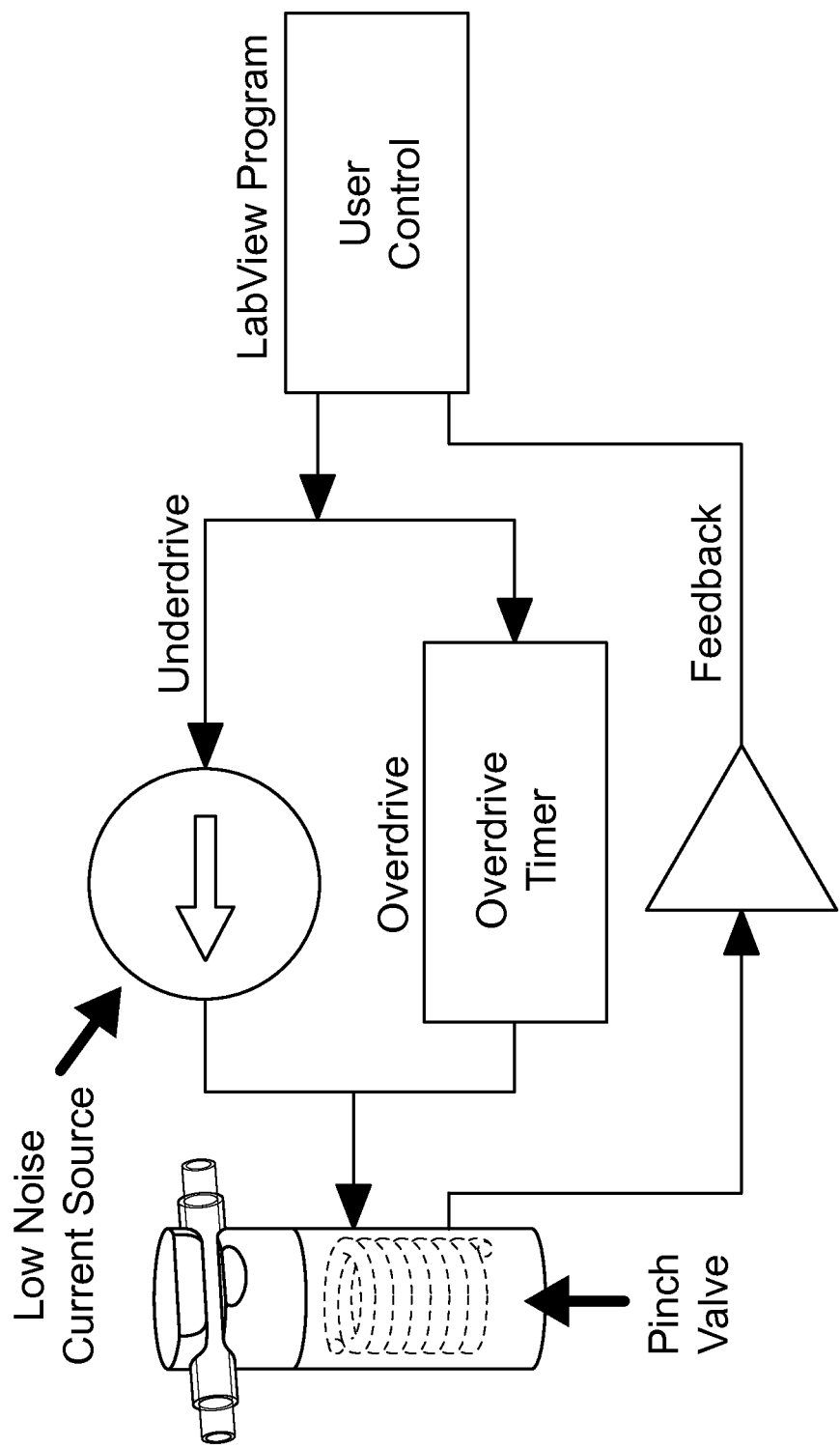
FIG. 10 depicts, in accordance with an embodiment of the invention, a pinch valve driver circuit. The valve is initially driven at 24 VDC for 164 ms (Overdrive mode). Once the valve closes, the power is reduced drastically to minimize stray magnetic fields and overheating (Underdrive mode).

Merely by way of non-limiting example, the pinch valve 300 can be configured as demonstrated in FIG. 9. The valve can include a stainless steel body 301, a spring force adjustment mechanism 302, a spring 303, a solenoid 304, a plunger 305, and a molded plastic head 306. The device can be configured such that the spring 303 applies force to the plunger 305, which in turn pinches a hose 600, as shown in FIG. 9. The force applied by the plunger on the hose can be regulated, thereby regulating the flow of liquid into and out of a reaction chamber, such as the reaction chambers 101 and 210 depicted in FIGS. 8 and 15, respectively.

Pinch Valve Modification

The PHIP method requires nearly three times more pressure than a commercially available pinch valve's rating. In order to increase the valve's pressure rating, the inventors increased the hose wall thickness using a sleeve and increased the plunger's spring force on the hose & sleeve. An exemplary hose 601 and sleeve 602 configuration 600 is demonstrated in FIG. 9. The sleeve can be made of a short section of flexible plastic hose with a ⅛" wall at the pinching point (such as the product made by Mcmaster, USA). This type of plastic has very good tensile strength and it is particularly resistant to tearing and delaminating. The force applied to the plunger was increased by compressing the plunger's spring to its maximum.

Valve Driver Circuit

Figure 11:
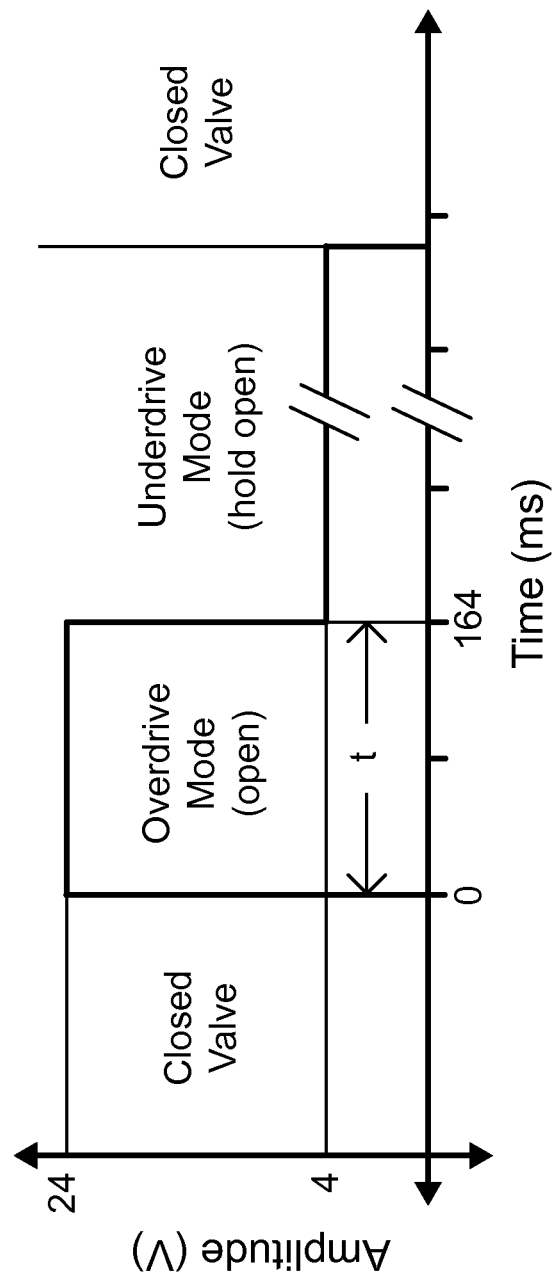
FIG. 11 depicts, in accordance with an embodiment of the invention, a pinch valve driving waveform. The overdrive period feeds 24 VDC to the solenoid for 164 ms. Then, the underdrive period supplies a low noise power sufficient to keep the valve's plunger off the hose.
Figure 12:
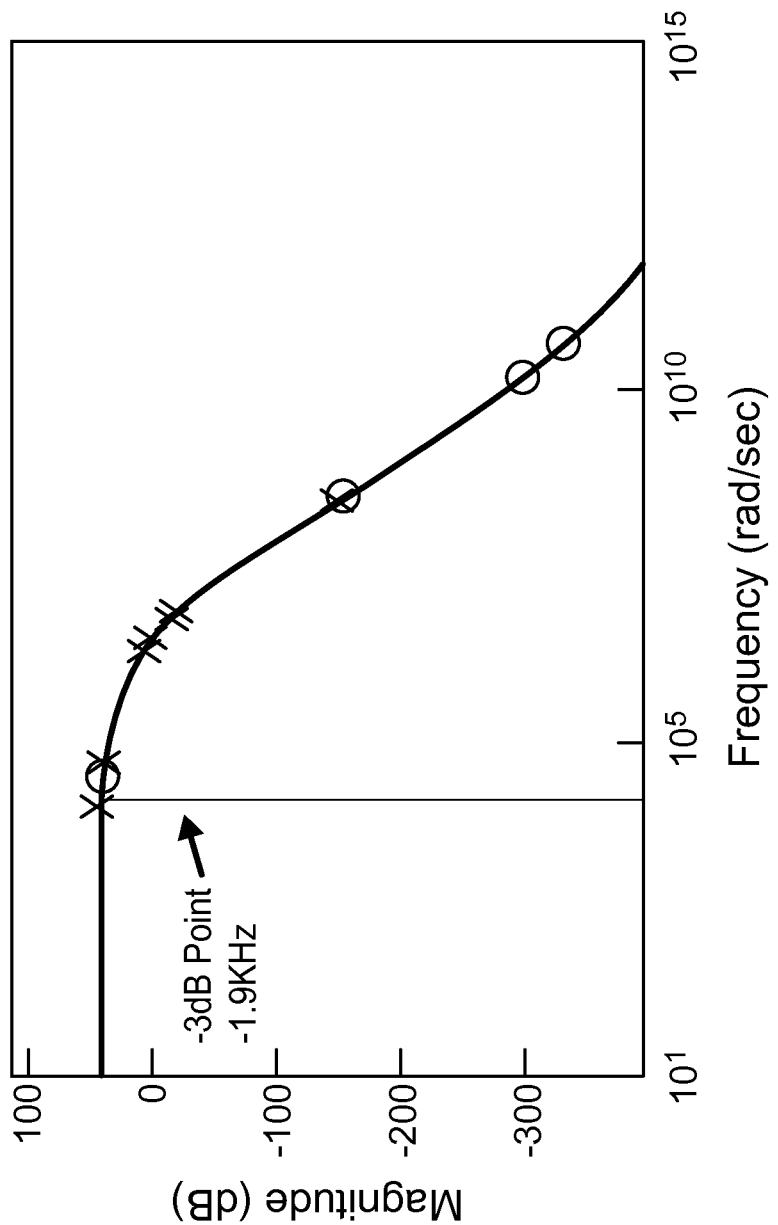
FIG. 12 depicts, in accordance with an embodiment of the invention, Equation (3) frequency response with zeros (o) and poles (x). The −3 dB point is near 1.9 KHz where the signal power drops below ½.

The inventive pinch valve circuit demonstrated in FIG. 10 serves as an improvement over unmodified pinch valves. The circuit provides additional power to allow the valve's plunger to overcome the increased force exerted on the plunger by the pinch force spring (Overdrive mode), while preventing stray magnetic fields from interfering with $B_o$, and minimizing valve body overheating (Underdrive mode) (FIG. 11). The circuit includes the following: 1) Current sink, 2) Overdrive Timer, 3) Valve feedback, and 4) Temperature sensor. In addition, the inventors employed various Matlab toolboxes to develop the small signal model for the current sink circuit, and consequent simulations result in the complete input/output TF ($I_o/V_{in}$) shown in equation (1).

$$TF = \frac{I_o}{V_i} = \frac{TF_1(s) * TF_2(s)}{R_{sense}} \tag{1}$$

Where $I_o$ is the current through the solenoid ($V_o/R_{sense}$), $V_i$ is the voltage reference, $TF_1$ is the active low pass filter TF, $TF_2$ is the current sink TF, $R_{sense}$ is the current sense resistor.

During the Underdrive mode, the current sink circuit provides the valve with a stable and low noise source of power that minimizes stray magnetic fields. The circuit was initially used as the power source for Bo in this PHIP instrument.

During the Overdrive mode, the circuit assists the pinch valve plunger to overcome the additional spring force applied to the plunger to keep the valve closed. The overdrive timer is activated when the valve is initially turned on by the rise of a transistor-transistor logic (TTL) pulse from the instrument. The timer is a one shot/monostable circuit that controls the power fed to the valve's solenoid through a metal-oxide-semiconductor field-effect transistor (MOSFET).

In order to verify a valve's successful activation, the inventors developed a monitoring circuit based on the current drawn by the pinch valve solenoid. The circuit uses a comparator to detect the increase of solenoid current. Once the valve has been activated, the solenoid current is compared to a reference, and if the current value is above the reference, then the comparator's output rises, signaling the instrument that the valve has been exercised, equation (2).

$$\text{Feedback} = \begin{cases} 1 \text{ if } V_{Solenoid} \geq V_{Ref}, \\ 0 \text{ if } V_{Solenoid} < V_{Ref}. \end{cases} \quad (2)$$

The hyperpolarization process is sensitive to temperature. The inventors' design can monitor the ambient temperature through a precision temperature sensor, such as the LM35 (Texas Instruments, USA). The temperature data is fed to a data acquisition card (DAQ) in the instrument, displayed on the screen, and digitally stored for later retrieval.

The calibration of the circuit is a two-step process; 1) solenoid power & 2) valve feedback calibration.

An important factor to minimizing stray magnetic fields that may interfere with $B_o$ and overheating lies in reducing the power applied to the valve's solenoid once the valve is open. The inventors refer to this effect as underdriving the pinch valve. The underdrive is powered by very stable low noise current sink. The circuit calibration is as follows: 1) Exercise valve using LabView software, 2) on the circuit board, turn current potentiometer (P1) counterclockwise to the end, 3) turn P1 clockwise until valve physically disengages, 4) turn back P1 a whole turn, and 5) exercise valve again to test function.

Exercise the valve using the LabView software, turn feedback potentiometer (P2) until LabView's valve display shows green.

In order to verify the amount of the valve's magnetic field interference with Bo during the over/underdrive modes, the inventors measured the solenoid magnetic field strength using a magnetoresistive permalloy sensor LIS331DLH (ST Micro-electronics, USA) embedded in an iPhone 4 (Apple, USA) 3" above the valve's solenoid. The valve's body temperature was measured using the 62 Mini IR Thermometer (Fluke, USA) from 3" away.

Results

Increased Pressure Rating

The total wall thickness increase by the sleeve measured 14", decreasing the flow capacity by 20%. However, the valve's pressure capacity increased by 266%, from 30 pounds per square inch (psi) to 80 psi. In addition, the valve's life time increased because of the shorter sleeve compression travel. Since the pinch force on silicon tubing is linearly proportional to pressure, the inventors deduce that the initial force to pinch the silicon hose at 30 psi is 25N, while the force to pinch the silicon hose at 60 psi is 50N.

Low Noise Current Sink Model

Figure 14:
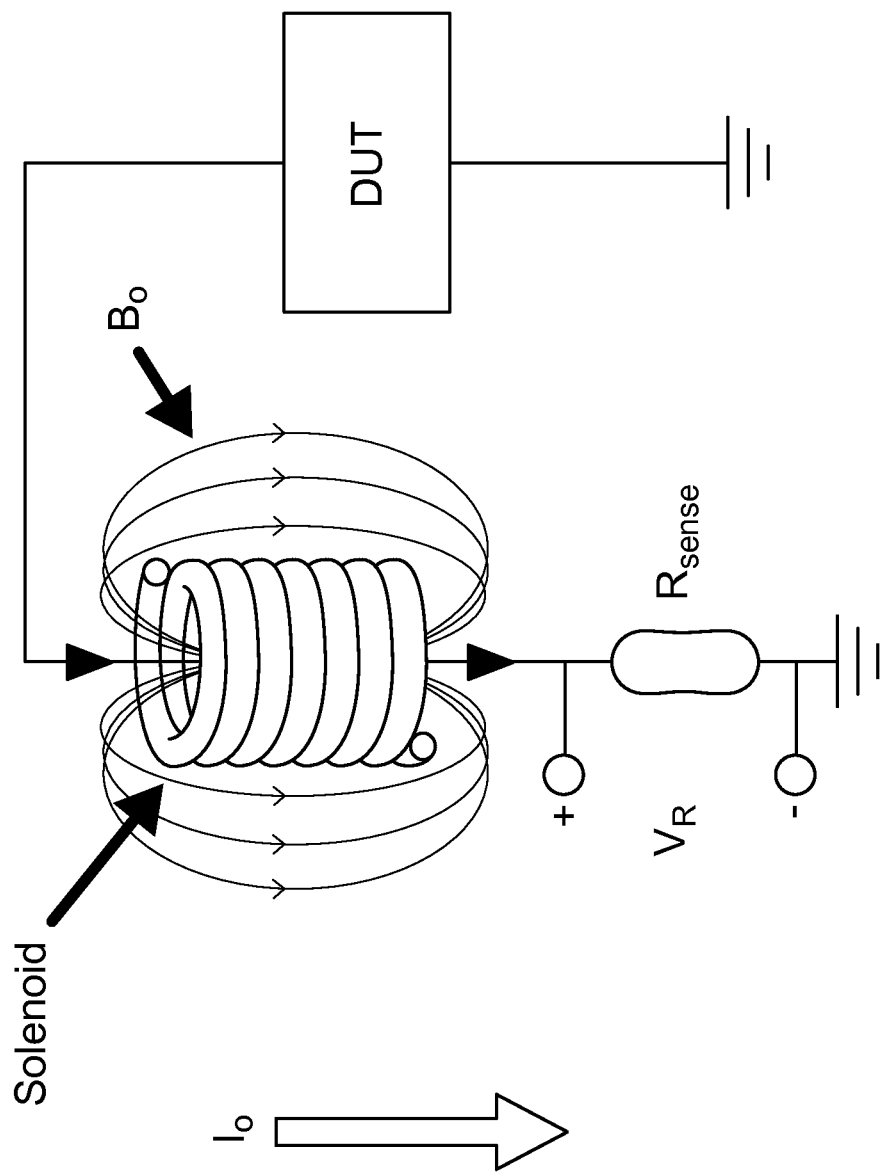
FIG. 14 depicts, in accordance with an embodiment of the invention, a Device Under Test (DUT) $i_n$ & $i_D$ measurement setup. The VCVS & VCCS are referred to as a DUT, $I_o$ is the current flow through the circuit and measured indirectly using Ohm's law. $V_R$ was measured using the multimeter 34411A.

From equation (1) and using a 0.1±0.1% resistor for $R_{sense}$ (Digikey, USA), yields equation (3). The plotting of zeros & poles show circuit stability with the dominant pole at 1.9 KHz (FIG. 14).

$$TF = \frac{I_o}{V_i} = 10 * TF_1(s) * TF_2(s) \quad (3)$$

$TF_1$, Active Low Pass Filter Model

A low noise, high stability voltage reference MAX6126 was used as a reference (Maxim Integrated, USA). The voltage reference output is further filtered by an active low pass filter, minimizing any residual electrical noise. Simulations yielded two zeros and three poles, equation (4).

$$TF_1(s) = \frac{V_{o1}}{V_{i1}} = \frac{(s-z_a)(s-z_b)}{(s-p_a)(s-p_b)(s-p_c)} \quad (4)$$

Where $V_{i1}=V_o$, $a_z$ & $b_z$ are the equation's zeros, and $a_p$, $b_p$, & $c_p$ are the equation's poles.

TF2, Current Sink Model

The resulting output voltage from the active low pass filter drives the gate of a MOSFET setup as a current sink. In order to maintain control of the MOSFET drain current, a low noise operational amplifier (Texas Instruments, USA) was setup in a negative feedback configuration. Simulations yielded three zeros and four poles, equation (5).

Overdrive Timer

The circuit is based on a one-shot, mono stable type circuit using a 555 timer (Texas Instruments, USA). The pulse $$TF_2(s) = \frac{V_{o2}}{V_{i2}} = \frac{(s-z_a)(s-z_b)(s-z_c)}{(s-p_a)(s-p_b)(s-p_c)(s-p_d)} \quad (5)$$

Where $V_{i2}=V_{o1}$ & $V_{o2}=V_{out}$, $a_z$, $b_z$, & $c_z$ are the equation's zeros, and $a_p$, $b_p$, $c_p$, & $d_p$ are the equation's poles.

length was 164 ms, equation (6). Overdrive pulses ≤100 ms may not sufficiently long to overcome the actuator's inertia.

$$t_{pulse}=\ln(3)*RC$$

$$t_{pulse}=\ln(3)*150K\Omega*1\ \mu F=164\ ms \quad (6)$$

Valve Magnetic Field & Temperature

During Underdrive mode, the magnetic field 3" above the pinch valve measured 10 μTesla (T)±0.1 μT, with no measurable valve body temperature increase. During Overdrive mode, the magnetic field measured 43 μT±0.1 μT. At continuous Overdrive mode (long pulse), the temperature measured 27.8° C. at activation and 82.3° C. at turn off, at a rate of $$0.1\frac{°C.}{\sec}.$$

This experiment was stopped at 82.3° C., as temperature continued to rise, risking the meltdown of the valve's plastic head.

Discussion

The inventors calculated the TF for the underdrive mode circuit and examined its frequency response. Frequency response analysis revealed that the circuit is stable with a dominant pole at 1.9 KHz. A much lower frequency pole can be achieved by including passive low pass filter at the voltage reference output, thus smaller magnetic noise. However, the valve's highest magnetic field strength was found to be small, 43 µT, or 1/42 of $B_o$, making further magnetic field noise improvements unnecessary.

The inventors also calculated the optimal overdrive pulse length (164 ms) and examined the large temperature rise for a long overdrive pulse. The inventors showed that a long overdrive pulse (≥10 min) and the large rate of temperature increase $$\left(0.1 \frac{°C}{sec}\right)$$

observed, may result in overheating and the melting of the valve's molded plastic head.

The temperature sensor placed on the board has become less important, as more accurate fluid temperature measurements are available elsewhere in the PHIP instrument.

Finally, the inventors have shown the addition of a plastic sleeve at the pinch point increases the valve's pressure rating by 266%. One of skill in the art would readily appreciate that the PHIP method applied to future precursors may require higher working pressures, and the pinch valve's pressure rating may be increased further by increasing the sleeve wall thickness, at a lower flow capacity and limited hosing life time.

Conclusion

The use of a disposable hosing for sterile sample management for the inventive PHIP method instrument prototype was designed and implemented. The use of a commercial set of pinch valves for the capture, process, and delivery of samples, was accomplished by modifying the pinching mechanism and valve's solenoid driving circuitry. The mechanism modification centered in the addition of a ¼" wall thickness plastic hose sleeve at the pinch area. The circuitry driving the solenoid modified the power fed to the solenoid in a two-step process. The first step provided the solenoid with 24 VDC to overcome the pinch spring force, which was compressed to its limit in order to keep the hose & sleeve pinched and stop flow. The second step provided the solenoid with a low noise, high stability source of power using a current sink. This current sink minimized stray magnetic fields that may interfere with Bo during the exercised of the pinch valve and minimized overheating that may destroy the valve's plastic head. The current sink circuit stability and frequency response was confirmed by developing a TF model using Matlab.

Example 3

Improved PHIP Polarization Using a Precision, Low Noise, Voltage Controlled Current Source Overview As indicated above, existing parahydrogen induced polarization (PHIP) instrumentation relies on magnetic fields to hyperpolarize substances. Required magnetic fields are generated by energizing a solenoid coil with current produced by a voltage controlled voltage source (VCVS), also known as a power supply. A VCVS lacks the current regulation necessary to keep magnetic field fluctuations to a minimum, which results in low PHIP polarization.

A voltage controlled current source (VCCS) is an electric circuit that generates a steady flow of electrons proportional to an input voltage. A low noise VCCS provides the solenoid current flow regulation necessary to generate a stable static magnetic field ($B_o$). The design and implementation of a low noise, high stability, VCCS for magnetic field generation with minimum variations is demonstrated herein below and in the referenced figures. The inventors demonstrate herein that a precision, low noise, voltage reference driving a metal oxide semiconductor field effect transistor (MOSFET) based current sink, results in the current flow control necessary for generating a low noise and high stability $B_o$. The description provided below 1) compares current stability for ideal VCVS and VCCS models using transfer functions (TF), 2) develops the inventive VCCS design's TF, 3) measures the inventive VCCS design's thermal & 1/f noise, and 4) measures and compares hydroxyethyl-propionate (HEP) polarization obtained using a VCVS and the inventors' VCCS. The hyperpolarization of HEP was done using a PHIP instrument developed in the inventors' lab. Using the inventors' VCCS design, HEP polarization magnitude data show a statistically significant increase in polarization over using a VCVS.

Introduction

The current flow generating a static magnetic field ($B_o$) in a PHIP instrument has been discussed previously, but in most instances attention has been directed towards the manual control of current using and feedback from Hall sensors placed near the solenoid generating $B_o$. The current produced by a VCVS often shows inherent changes in current stability, which is observed as magnetic field noise in $B_o$. This noise often changes rapidly such that manual corrections become insufficient, altering the $B_o$ and changing the nuclear resonance frequencies. In turn, this negatively affects the maximum polarization achieved.

Voltage controlled current sources (VCCS), generally known as current sources, are the foundation of electronic circuit design. They provide the basic current and voltage conditions for electronic circuits to operate. Originally, current sources were designed using resistors. However, their use resulted in poor accuracy and stability due to size limitations, temperature instability, and manufacturing variations. A current regulator diode (CRD) was developed in 1958 (Crystalonics Inc, USA). This diode was a small single component that produces constant current flow regardless of changes in power supply voltage. Then, in 1964, Robert Wildlar developed precision current source references which led to the µA702 design, the first commercial monolithic operational amplifier (OA). VCCS designs are also popular in biomedical imaging, more specifically electrical impedance tomography (EIT). EIT VCCS designs are mainly based on improvement with the Howland VCCS design, their working frequencies vary from as low as 10 Hz to as high as 2.74 MHz and currents from 500 µA-5 mA. The inventors' VCCS design differs from Howland based VCCS designs in 1) working frequency is 0 Hz, 2) High currents (≥500 mA), 3) low noise (≤10 ppm), and 4) low drift (≤15 ppm for 70 hrs). Previous research in PHIP instrumentation has also produced a VCCS design with high currents, but may have much larger noise and drift, mainly due to components values producing large thermal noise and the lack of transient protection components. The development of quieter, more stable current sources continues to this day with the development of the high-stability, laser-trimmed, thin-film resistors, which allow for current source designs with excellent initial accuracy, a very low temperature coefficient, and low noise level. These developments have been incorporated in the design of one of today's most precise and stable voltage reference ICs, the Maxim MAX6126 (device used in this VCCS design), a device with a wide operational temperature range, ultra-low noise & temperature compensation, high accuracy, and force/sense outputs.

In addition to the theoretical & numerical simulations, and noise measurements, the inventors herein demonstrate comparative Hydroxyethyl-propionate (HEP) (Sigma-Aldrich, USA) $^{13}$C hyperpolarization results using a VCVS & VCCS. The models described are based on transfer functions (TF), which supply the basis for finding the circuit response characteristics without solving differential equations. First, the inventors developed the ideal VCVS & VCCS TFs and impulse responses, effectively demonstrating the VCCS' immunity to current flow fluctuations. Next, using Matlab (Mathworks, USA) simulations the inventors develop a VCCS design's TF, which is estimated using the method of open-circuit time constants, followed by the system's output current/input voltage $$\left(\frac{I_o}{V_{in}}\right) TF.$$

Then, the inventors show the VCCS' thermal and & 1/f (flicker) noise measurements, which are the largest contributors to current fluctuations. Finally, the inventors present the HEP $^{13}$C hyperpolarization data showing a statistically significant increase in polarization using the VCCS developed in the inventors' lab.

Methods

In circuit analysis and according to Watt's law, an ideal VCVS regulates voltage. A VCVS maintains a given voltage difference between its terminals independent of the current drawn. An ideal VCCS regulates current. A VCCS maintains a given current through its terminals independent of the voltage across its terminals. Any circuit can be modeled for analysis as a combination of voltage sources, current sources, and impedance elements. These models further simplify with the aid of Laplace transformations and TFs for circuit analysis in the s-Domain. The inventors employed various Matlab toolboxes to develop the small signal models, and consequent simulations result in the circuit's input voltage/output current ($I_o/V_{in}$) TF.

Ideal Voltage Controlled Sources Model

First, the inventors developed the TF of an ideal VCVS & VCCS powering a solenoid (L) in the s-Domain. Then, the inventors compared the TFs' susceptibility to external influences by applying an impulse to the TFs. An impulse is defined as an infinitely short and infinitely large pulse.

Actual VCCS Model Development

Figure 13:
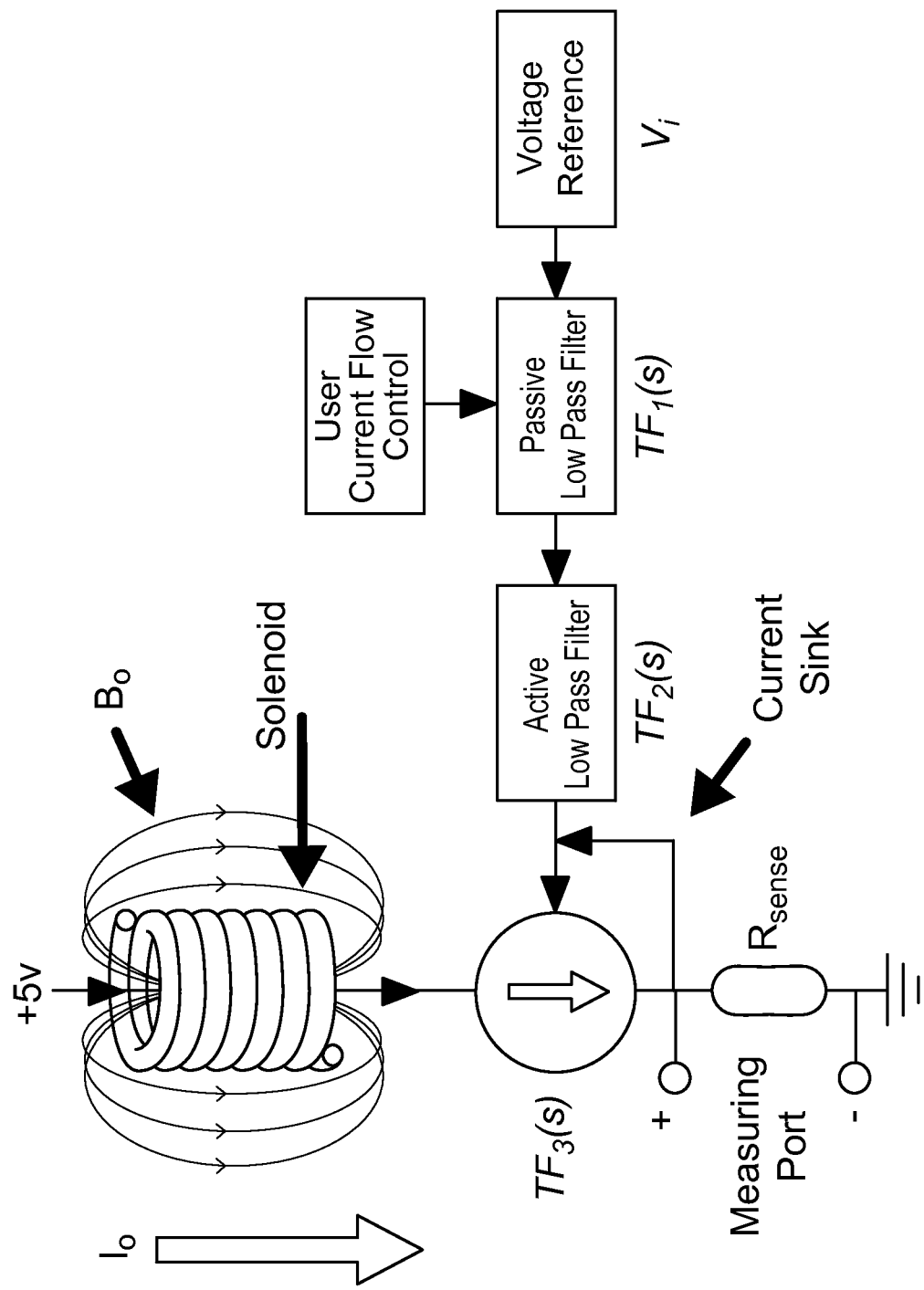
FIG. 13 depicts, in accordance with an embodiment of the invention, a VCCS design block diagram. A TF model was developed for each circuit component. The $TF_{vccs}$ is the product of each TF, which ultimately is used to characterize $I_o$ and $B_o$. The solenoid was designed for an input power of +5V.

The inventors begin by describing the VCCS components, which include 1) an ultra-high precision, ultra-low noise, series voltage reference, 2) A passive low pass filter, 3) An active low pass filter, and 4) A MOSFET current sink and OA with negative feedback (FIG. 13). The passive low pass filter uses a ten-turn potentiometer as a voltage divider to adjust $I_o$. Then, the output voltage is filtered by an active low pass filter, minimizing any residual noise. Finally, the resulting output voltage controls a MOSFET setup as a current sink. In order to maintain control of the MOSFET drain current, an OA is setup in a negative feedback configuration. Once the individual TFs are found, they are combined in a complete TF for the entire circuit (eq.1).

$$TF_{vccs} = \frac{I_o}{V_i} = \frac{TF_1(s) * TF_2(s) * TF_3(s)}{R_{sense}} \quad (1)$$

Where $TF_{vccs}$ is the complete model's TF, $I_o$ is the current through the solenoid ($V_o/R_{sense}$), $V_i$ is the voltage reference, $TF_1(s)$ is the passive low pass filter TF, $TF_2(s)$ is the active low pass filter TF, $TF_3(s)$ is the current sink TF, $R_{sense}$ is the current sense resistor.

Current Noise ($i_n$) & Long Term Drift ($i_D$)

The inventors compared $i_n$ & $i_D$ from their VCCS design and an off-the-shelf VCVS (Acifica Inc, Mastech HY3003D-3, USA). $B_o$ and the Larmor frequency drift ($F_A$) for $i_n$ & $i_D$ were calculated using the BiotSavart law and the Larmor frequency equations. The inventors setup an experiment to collect $i_n$ & $i_D$ for each device (FIG. 14) as follows: 1) A solenoid was placed in series with a 1Ω±0.1% current sense resistor ($R_{sense}$), the sense terminals of R were used as a measuring port; 2) the current generated by the device under test (DUT) flowed through the solenoid and the current flow indirectly measured using Ohm's law; 3) $V_R$ was measured using a 34411A digital multimeter (Agilent, USA) at the 1 v range with a 1.5 ppm resolution. Four sets of data were collected comparing the DUT's $i_n$ & $i_D$. For each device, $i_n$ & $i_D$ data was collected at 1.6 k samples/s for 30 seconds and at 0.2 Hz for 70 hrs respectively.

Current Thermal & 1/f Noise

The inventors collected thermal and 1/f noise for their VCVS design using the Agilent 35670A FFT Dynamic Signal Analyzer (Agilent, USA). The 35670A's 90 dB dynamic range and ±0.15 dB accuracy makes the instrument the standard for thermal & 1/f noise measurements. The temperature within the PHIP instrument prototype was controlled using a PXR4 proportional-integral-derivative (PID) controller (Fuji Electric, Japan), with a 0.5° C. accuracy. The current was adjusted manually using a 100Ω potentiometer in the VCCS circuit board and measured indirectly by Ohm's law using the 34411A. The experiment was setup by connecting the 35670A's input directly to the VCCS' measuring port. Data was captured from 0 Hz to 1.6 KHz, with 401 points, and 100 averages. The VCCS was characterized over the temperature and current. Temperature was varied from 40° C. to 70° C. in 2° C. increments, and current from 50 ma to 900 ma in 50 ma increments, for a total of 255 points. Then, the 1/f rms ($I_{n,rms}$) (eq. 5) and peak-to-peak $I_{n,pp}$ noise was calculated.

Hydroxyethyl Propionate Hyperpolarization

The PHIP hyperpolarization experiment for producing $^{13}$C hyperpolarized HEP was setup using a PHIP instrument developed in the inventors' laboratory (FIG. 15). HEP is the hydrogenated Hydroxyethyl acrylate (HEA) (CAS:676071, Sigma-Aldrich, USA) substrate used as a precursor in the PHIP method. $^{13}$C hyperpolarized HEP has been used in the past as a contrast agent for the perfusion mapping of pig myocardium. The goal of the experiment was to produce $^{13}$C hyperpolarized HEP using a VCVS and a VCCS for generating the $B_o$ in the inventors' PHIP instrument. Then, the polarization obtained was compared for each DUT. The experiment performed for each DUT was as follows: 1) The DUT was installed in the PHIP instrument, 2) An HEA solution was prepared, 3) Each sample was run with the PHIP instrument's polarization automated process, 4) Each HEP sample was collected and its polarization measured in a 9.4 T scanner (Bruker BioSpin MRI/MRS, USA).

HEA Solution Preparation

A 40 mL solution of deuterium oxide ($D_2O$) was used to dissolve 10 mM of Hydroxyethyl acrylate-1-$^{13}C$, 2,3,3-d3 (HEA) and 2 mM of Wilkinsons catalyst Rh norbornadiene bisphosphine (CAS:36620-11-8, Sigma-Aldrich, USA). The solution yielded 13 samples of 3 ml.

PHIP Instrument Polarization Process 3 mL of HEA solution was inserted into the PHIP instrument through a syringe 205 and the preprogrammed Labview (National Instruments, USA) automation software began the polarization process. In the PHIP process (FIG. 15), the sample was heated for 45 seconds by conduction using an aluminum block 204 to 45° C. While the sample was heated, the reaction chamber 210 was filled with 95% para-Hydrogen (p-$H_2$) gas at 3.5 bar produced using a ARS-4HW p-$H_2$ generator (Advanced Research Systems, USA). Next, the sample was pushed into the reaction chamber 210 and the HEA was hydrogenated to HEP with the aid of the catalyst. During the hydrogenation process, the sample was irradiated with a radio frequency (RF) sequence with a 3 sec decoupling time using a saddle type coil ($B_1$), and the para-hydrogen spin order was transferred to the adjacent $^{13}C$ nuclei. Finally, the sample was ejected out of the instrument 210 and captured in a syringe 206.

For reference, a full list of the components represented in the inventive system 200 of FIG. 15 are as follows: pinch valves 201, 211, 212, 213, and 214; hosing 202 for introducing parahydrogen into the reactor 210; hosing 203 for introducing a sample into the reactor 210; a sample heater 204 (with grooves for the hosing as describe above); a sample inlet port 205; a sample outlet port 206; a syringe 215 for introducing a sample; a syringe 216 for removing a hyperpolarized sample; a pressure gauge 209; a parahydrogen tank 207; and a nitrogen tank 208.

Measuring HEP Polarization

The HEP sample polarization was measured with a 9.4 T Bruker Biospin Scanner using a 90° hard pulse using a Helmholtz single resonance 13c coil. The signal was acquired with a 20 kHz spectral width at the $^{13}C$ carbonyl resonance frequency. The actual polarization was calculated from the Boltzmann signal of sample one.

Results

VCVS Model

Figure 16B:
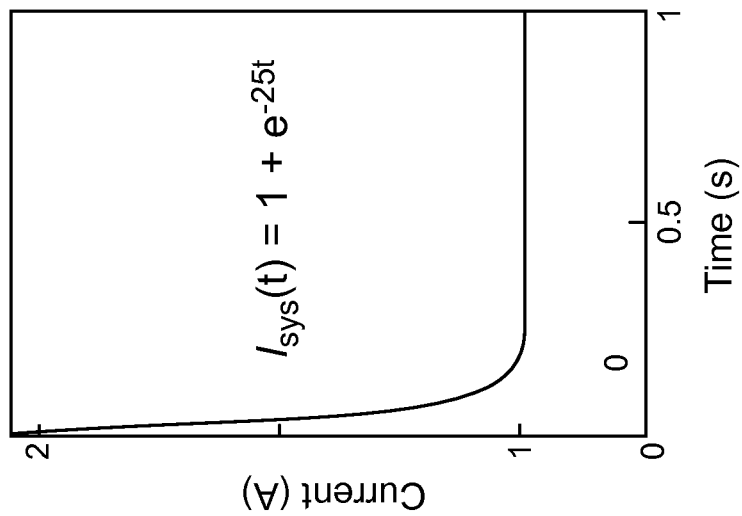
FIG. 16 depicts, in accordance with an embodiment of the invention, a VCVS is incapable of generating a stable current flow I(s), leading to an unstable $B_o$, while the VCCS produces a stable I(s), thus a stable Bo. VCVS & VCCS transfer functions with an impulse response were developed and tested across a resistor ($R_{sense}$), as Kirchhoff's law dictates $i_{sys}(t)=i_R(t)$. a) Ideal VCVS test setup, b) VCVS impulse response, current flow after a disruptive impulse measured at $R_{sense}$, c) Ideal VCCS test setup, d) VCCS impulse response, current flow after a disruptive impulse measured at $R_{sense}$.
Figure 16A:
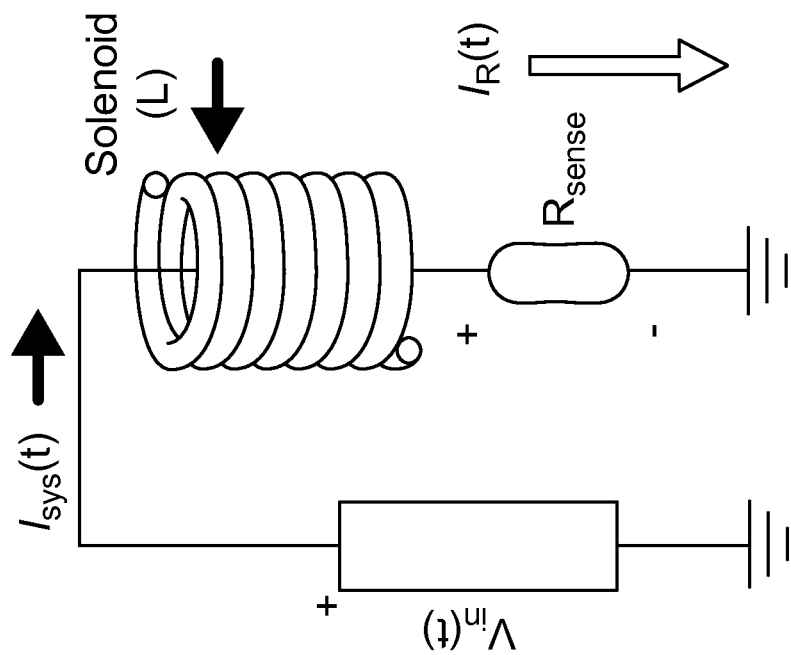

In order to obtain the VCVS circuit setup model (FIG. 16a), the inventors derived the current of the system ($i_{sys}(t)$) with disruptive noise, or impulse pulse ($\delta(t)$) (eq. 2). The inventors began by deriving the voltage at the resistor ($V_R(s)$) in the s-Domain, using the voltage divider rule and ohm's law (eq. 4). Next, the inventors applied an impulse pulse (eq. 5) to $V_R(s)$ (eq. 6). Then, the inventors applied the inverse Laplace transformation to $V_R(s)$ (eq. 7) and substituted (eq. 8). The inventors obtained current through R with an impulse pulse (eq. 9) in the time-Domain. The inventors continued substituting the current through R with an impulse pulse (eq. 9) into the $i_{sys}(t)$ (eq. 10) and constants (eq. 11) (FIG. 16b). The VCVS' $i_{sys}(t)$ changes exponentially in the presence of a disrupting impulse pulse, making a VCVS design a poor choice for generating a stable $B_o$.

$$i_{sys}(t) = i_R(\infty) + i_R(t) * \delta(t) \quad (2)$$

Where $i_R(\infty)$ is the current steady state, $i_R(t)$ is the function of the current flow at the resistor (R), and $\delta(t)$ is the impulse pulse applied to the circuit.

VCCS Model

Figure 16D:
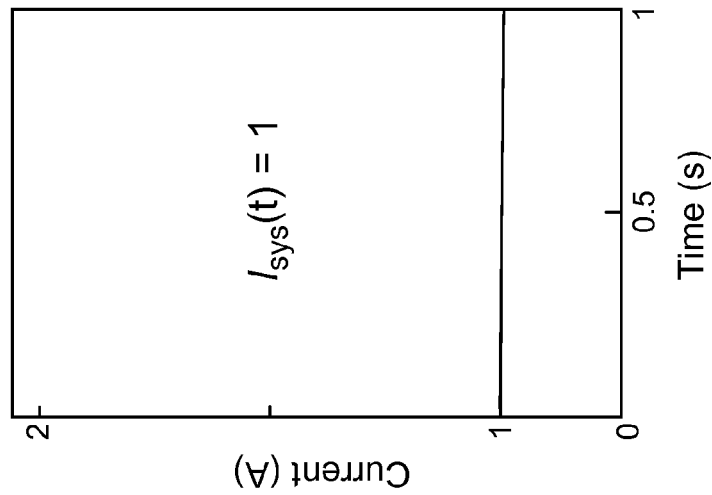
Figure 16C:
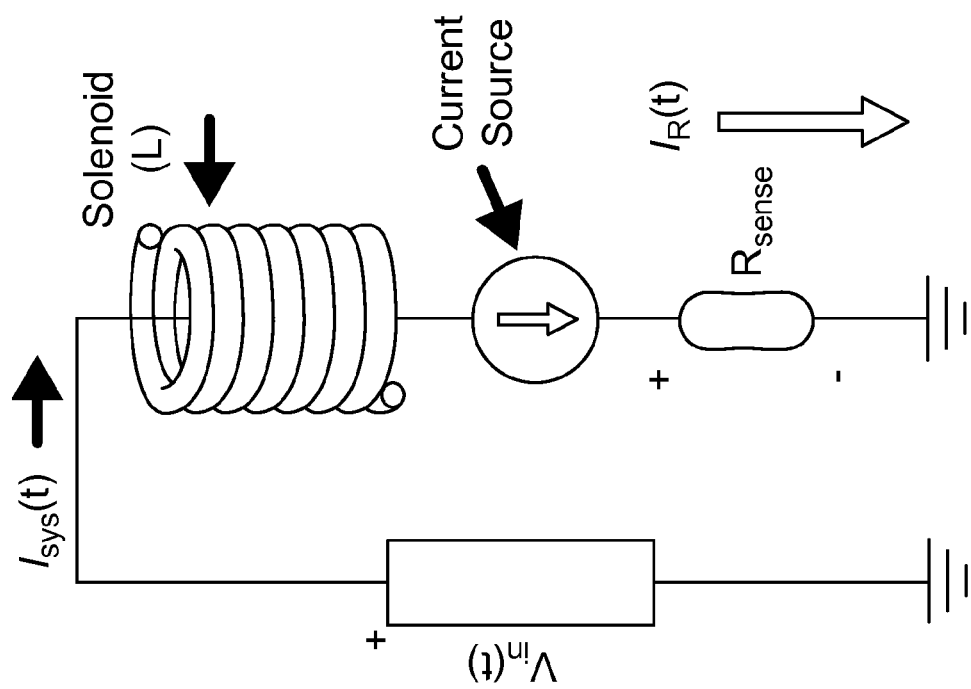

Similar to the VCVS derivation, the inventors derived a VCCS circuit setup model (FIG. 16c). Using Kirchhoff's law, the VCCS current flow is the same at any point in the circuit (eq. 3) (FIG. 16d). The VCCS' current flow is a given constant, thus an ideal VCCS' output current is immune to noise, making this design a good choice for generating a stable $B_o$.

$$i_{sys}(t) = i_{in}(t) = i_R(t) = 1 \text{ Amperes} \quad (3)$$

Actual VCCS Model

Figure 17:
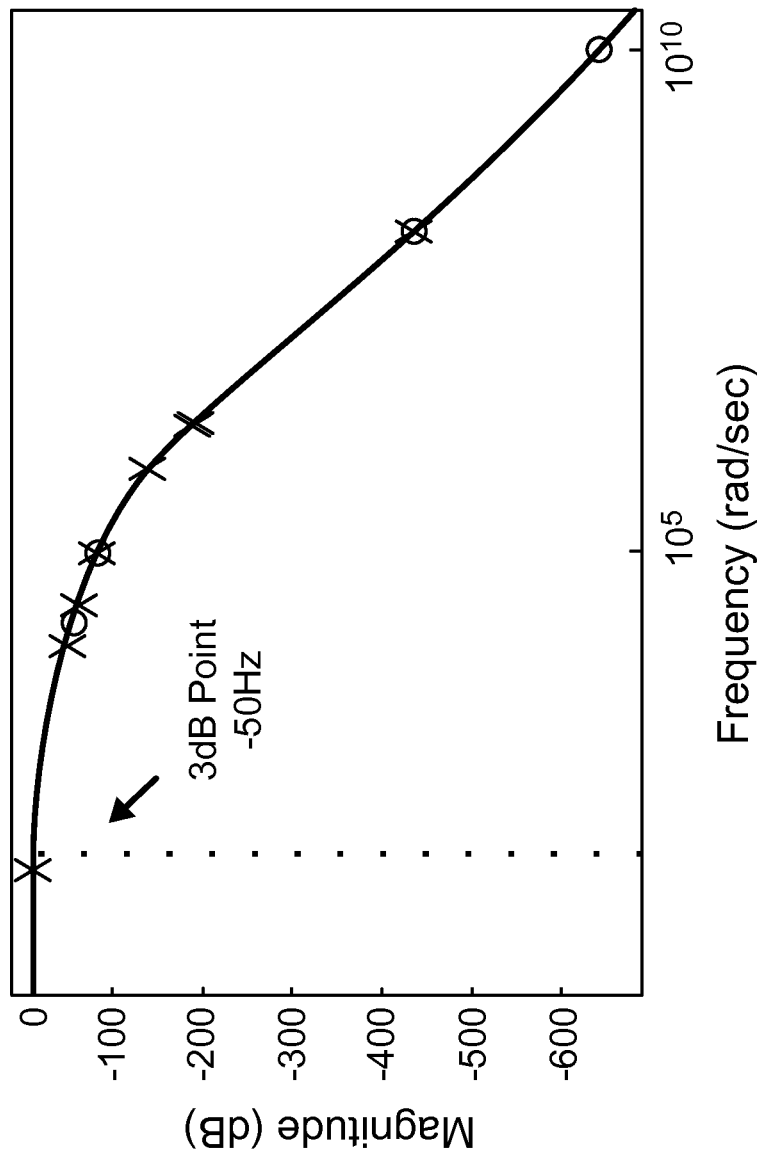
FIG. 17 depicts, in accordance with an embodiment of the invention, Equation (14) frequency response with zeros (o) and poles (x). The 3 dB point is near 50 Hz where the signal power drops below ½.

The individual VCCS component TFs (FIG. 13) were found for: 1) passive low pass filter (eq. 12), 2) active low pass filter (eq. 13), and 3) MOSFET current sink (eq. 14), and the complete frequency response (FIG. 17). The VCCS design is characterized $$V_R(s) = V_{in} * \frac{R}{sL + R} \quad (4)$$

$$\mathcal{L}\{\delta(t)\} = 1 \quad (5)$$

$$V_R(s) * 1 = V_{in} * \frac{1}{s + \frac{R}{L}} * 1 \quad (6)$$

$$\mathcal{L}^{-1}\{V_R(s) * 1\} = V_{in} * \mathcal{L}^{-1}\left\{\frac{1}{S + \frac{R}{L}}\right\} \quad (7)$$

$$i_R(t) = \frac{V_R(t)}{R}, e^{a*t} = \mathcal{L}^{-1}\left\{\frac{1}{S - a}\right\} \quad (8)$$

$$i_R(t) * \delta(t) = V_{in} * e^{-\frac{R}{L}t} \quad (9)$$

$$i_{sys}(t) = i_R(\infty) + V_{in} * e^{-\frac{R}{L}t} \quad (10)$$

$$i_{sys}(t) - 1 + e^{-25t} \quad (11)$$

Where the $i_R(\infty)=1$ A, $V_{in}=1$V, L=40 mH, & R=1Ω.

by the TF's dominant pole and damping ratio. The dominant pole ($\omega_d$) determines the low pass filter prevalent cut-off frequency and the damping ratio ($\zeta$). $\zeta$ describes how quickly a disturbance decays after being applied to the inventors' design. A $\zeta=1$ means short decay, while $\zeta=-1$ means a long decay. The design's complete TF shows a $\omega_d=49$ Hz & a $\zeta=0$, failing stability using the routh test with four negative real roots. The passive low pass filter's TF (eq. 12) with $\omega_d=49$ Hz and a $\zeta=1$. The active low pass filter's TF is (eq. 13) with $\omega_d=1.893$ kHz and a $\zeta=1$. The current sink's TF (eq. 14) with $\omega_d=296$ Hz and a $\zeta=-1$.

$$TF_1(s) = \frac{V_{o1}}{V_{i1}} = \frac{(s - z_a)}{(s - p_a)(s - p_b)} \quad (12)$$

Where $V_{i1}=V_{in}$, $a_z$ is the equation's zero, and $a_p$ & $b_p$ are the equation's poles.

VCCS Load Correlation

The VCCS system TF model ($TF_{vccs}$) was solved for $I_o$ and evaluated at V, from 300 mV to 1V, with two different loads, $$TF_2(s) = \frac{V_{o2}}{V_{i2}} = \frac{(s - z_a)(s - z_b)}{(s - p_a)(s - p_b)(s - p_c)} \quad (13)$$

Where $V_{i2}=V_{o1}$, $a_z$ & $b_z$ are the equation's zeros, and $a_p$, $b_p$, & $c_p$ are the equation's poles.

$$TF_3(s) = \frac{V_{o3}}{V_{i3}} = \frac{(s-z_a)(s-z_b)(s-z_c)}{(s-p_a)(s-p_b)(s-p_c)(s-p_d)} \quad (14)$$

Where $V_{i3}=V_{o2}$ & $V_{o3}=V_{out}$, $a_z$, $b_z$, & $c_z$ are the equation's zeros, and $a_p$, $b_p$, $c_p$, & $d_p$ are the equation's poles.

1.5Ω & 4Ω. Then, the circuit's $I_o$ was measured under the same loads. $TF_{vccs}(I_o)$ data correlates with experimental data to 0.02% at 0 Hz.

VCCS Current Noise & Long Term Drift $B_o$ and the resonance frequency shifts for $^1H$ & $^{13}C$ were calculated using the BiotSavart law & the Larmor frequency equation.

Current Noise ($i_n$)—

Figure 18A:
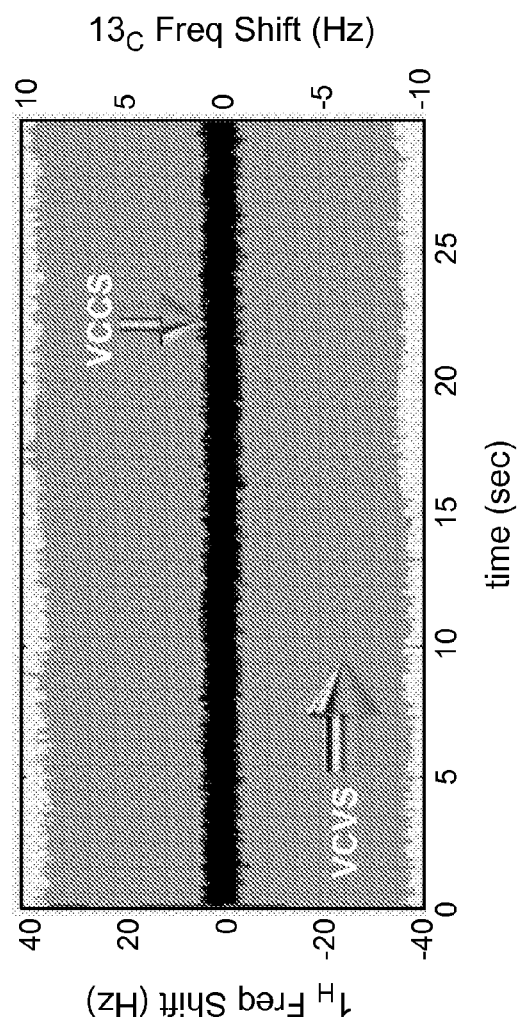
FIG. 18 depicts, in accordance with an embodiment of the invention, $B_o$ current noise & Drift. a) Resonance frequency shift caused by current flow noise ($i_n$). $i_n$ data was captured at 1.6 k samples/s for 30 seconds. VCVS' $i_n$ is depicted in a lighter shade, while VCCS' $i_n$ is depicted in a darker shade, b) Resonance frequency shift caused by current flow long term drift $i_D$. $i_D$ data was collected at 0.2 samples/s for 70 hrs. VCVS' $i_D$ is depicted in a lighter shade, while VCCS' $i_D$ is depicted in a darker shade.

VCVS showed a change in $i_n$ of ±31.6 Hz & ±7.97 Hz for $H_2$ & $^{13}C$ respectively, while the VCCS showed a change of ±4.1 Hz & ±1.03 Hz for $H_2$ & $^{13}C$, respectively (FIG. 18a).

Current Drift ($i_D$)—

Figure 18B:
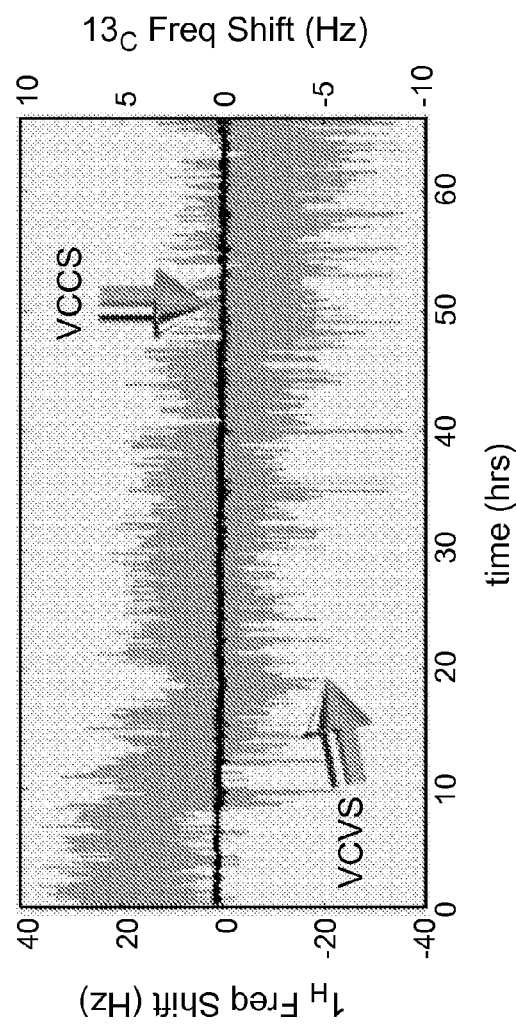

VCVS showed a change in $i_D$ of ±37.9 Hz & ±9.5 Hz for $H_2$ & $^{13}C$ respectively, while the VCCS showed a change of ±1.4 Hz & ±0.3 Hz for $H_2$ & $^{13}C$, respectively (FIG. 18b).

VCCS Current Thermal & 1/f Noise—

The average over all noise found was 22.5 μA±12.5 μA. The least noise was found at higher temperatures 10 μA, while the largest noise was at low temperatures 35 μA. Curve fitting was done using Matlab's Lowess model with a 25 span and a quadratic polynomial, resulting in R=0.74 (FIGS. 20a & 20b).

VCCS Thermal Noise—

The average thermal noise ($I_{tn}$) found was 125 nA $\sqrt{Hz}$ with-out noticeable changes over temperature (FIG. 19a).

VCCS 1/f Noise—

The 1/f rms current noise ($I_{n,rms}$) was 12 μ$A_{rms}$ (eq. 15), for $I_{tn}$=125 nA $\sqrt{Hz}$, $F_c$=1 KHz, $F_L$=0.1 Hz, and $F_H$=1.6 Hz, resulting in a peak-to-peak noise ($I_{n,pp}$) of 79.2 μ$A_{pp}$ (eq. 16).

$$I_{n,rms} = I_{tn}\sqrt{F_c * \ln\frac{F_c}{F_L} + (F_H - F_c)} \quad (15)$$

$$I_{n,pp} = 6.6 * I_{n,rms} \quad (16)$$

where $I_{n,rms}$ is the 1/f rms noise, $I_{tn}$ is the thermal noise voltage, $F_c$ is the 1/f corner frequency, $F_L$ is the lower frequency of the measurement, and $F_H$ is the upper frequency of the measurement, $I_{n,pp}$ is the 1/f noise peak to peak current and 6.6 is the rms to Peak-to-peak most used conversion factor.

HEP Hyperpolarization

Figure 21A:
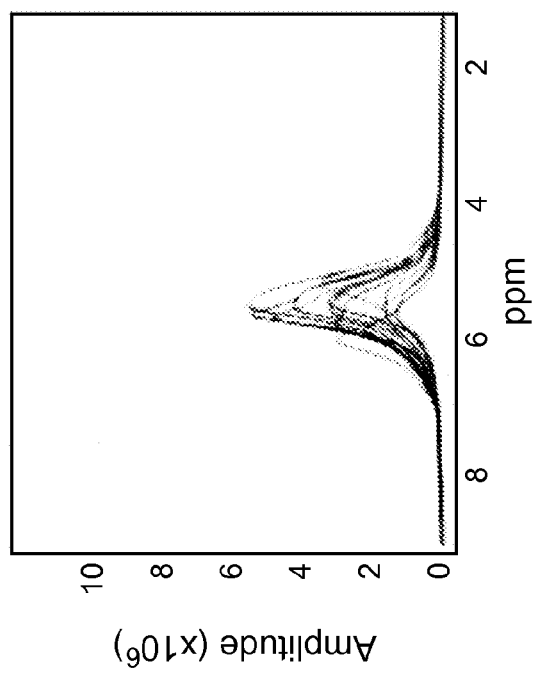
FIG. 21 depicts, in accordance with an embodiment of the invention, HEP polarization $^{13}C$ spectra using a Bruker 9.4 T scanner. a) VCVS $B_o$ driven polarization. b) VCCS $B_o$ driven polarization.
Figure 21B:
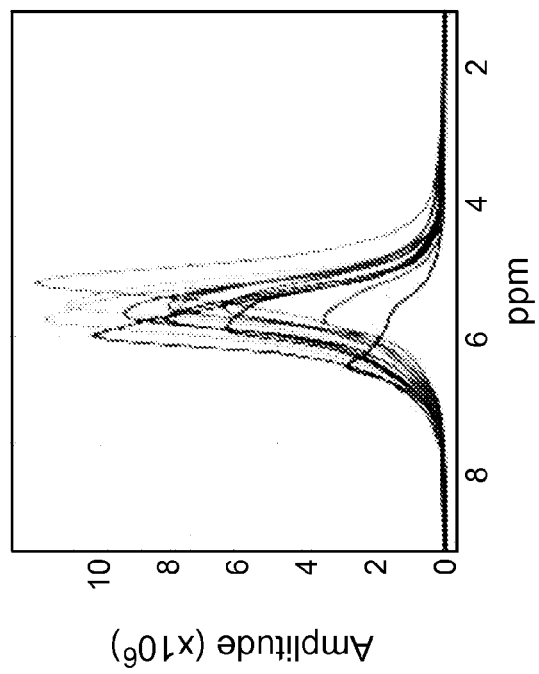

Finally, a total of 26 HEP polarization samples were collected, 13 samples for VCVS & 13 samples for VCCS. Spectra for VCVS driven $B_o$ (FIG. 21a) and spectra for VCCS driven $B_o$ (FIG. 21b). For each sample, volume & peak area were recorded, and peak area was corrected by volume. Then, the mean ($\bar{x}$), standard deviation (σ), and polarization percent were calculated. The maximum HEP polarization for the VCVS was 0.53%, while the VCCS was 1.1%. Unpaired t-test has shown that the data sets are statistically significant with a P=0.0004 and a σ=32.

Discussion

As demonstrated herein, the inventors have provided results for the implementation of a VCCS for increasing the $^{13}C$ hyperpolarization of HEP. The inventors deduced that the use of a low noise, high stability voltage reference driving a current sink generates a stable $I_o$ to 15 ppm, resulted in a stable $B_o$ for the $^{13}C$ hyperpolarization of HEP. This led to a new definition for the generation of a precision $B_o$ for hyperpolarization applications. This new approach is fundamentally different from the generation of $B_o$ using VCVS devices, which does not control the flow of current.

The inventors calculated the TF's solutions and examined the circuit stability. Although the circuit is stable at 0 Hz (where the circuit usually performs), the stability of the current sink section in the circuit begins to decreases at higher frequencies, thus the negative poles. More specifically, the instability resides at 380 kHz with a 200 kHz bandwidth and a peak gain of 2. Because of the dominant pole at 49 Hz, this characteristic should only affect $i_n$ & $i_D$ at a minimum beyond thermal and 1/f noise frequencies (≤1 kHz).

In addition, the inventors showed the VCCS current stability is slightly influenced by thermal noise, while 1/f noise plays a bigger role in polarization. However, one of skill in the art would readily appreciate that thermal noise may be further decreased by cooling the circuitry. Since 1/f noise is inversely proportional to temperature, 1/f noise may not be an issue, as the hydrogenation of a precursor is optimized at temperatures above 45° C., where 1/f noise tents to minimize.

One of skill in the art would readily appreciate that the inventors' definition of precision $B_o$ generation indicates new approaches, more specifically, the inclusion of parasitic capacitances and inductances for the development of a more accurate TF model, circuitry optimization using TFs, and board layout are likely to be particularly rewarding. Merely by way of example, in order to maximize circuitry efficiency, minimizing the amount of poles and including negative feedback will produce a more efficient circuit with less components and a lower in $i_n$ & $i_D$. Most importantly, the circuit will be more immune to external influences such as electrical noise and temperature changes.

Conclusion

The inventors have demonstrated a model of a VCCS for the generation of precision $B_o$ in PHIP instrumentation. The inventors' approach shows a lower $i_n$ and $i_D$ and a statistical significant increase in HEP polarization (P=0.0004) compared to previous methods of $B_o$ generation. The VCCS model, confirmed by experimental results with a 0.02% correlation at 0 Hz, shows that $i_n$ and $i_D$ are principally dependent on the control of current flow. Because of the reduction in $i_n$ and $i_D$, the inventors were able to achieve higher levels of polarization. Specifically, for 10 mM of HEA, 2 mM of catalyst solution, and the Goldman RF sequence, the HEP polarization increased 54% than using other methods of $B_o$ generation.

Example 4

LabVIEW Instrumentation Control Software for RF Transfer para-Hydrogen Induced Polarization Overview Another aspect of the invention involves National Instruments (NI) LabVIEW software for the control of hyperpolarization instrumentation, or other applications requiring automated control of gas flow and time sensitive chemical reactions. The hyperpolarization of cellular metabolites for molecular imaging is a challenging process, which requires precise control of: 1) chemical reaction timing, 2) gas flow, 3) monitoring of a magnetic field (Bo), radio frequency irradiation, 4) chemical reaction temperature, and 5) gas pressures. Current Parahydrogen Induced Polarization (PHIP) method instrumentation lacks the software versatility and graphical user interface to control and modify the PHIP process. The description provided below indicates how a LabVIEW based software application allows for the precise control over the delivery and manipulation of gasses and samples, while simultaneously monitoring gas pressures, environmental temperature, and Radio Frequency sample irradiation. The implementation of this software provides a fast prototyping for evaluating PHIP method instrumentation.

Introduction

LabVIEW, a high level graphical programming language, efficiently adapts to hyperpolarization process challenges and allows for a more natural intuitive man-machine interaction than text based languages. Furthermore, as hyperpolarization of metabolites difficulties arise, LabVIEW's hardware control versatility and easy to program graphical user interface (GUI), reduce costs associated with the hyperpolarization process automation. In reviewing the literature, no LabVIEW software applications in para-Hydrogen Induced Polarization (PHIP) instrumentation have been published.

Methodology

LabVIEW

The LabVIEW software provides a graphical application development environment developed by NI in 1986 for Apple Macintosh. LabVIEW is composed of several sub-tools targeted at making the development and prototyping of instrumentation applications very simple, flexible, and efficient. This prototype was developed with software flexibility in mind, allowing for easy and intuitive changes to its graphical code, which makes LabVIEW a very versatile tool for hyperpolarization research purposes.

Signal Acquisition

The signals acquired using the techniques described herein below are: temperature, pinch valve status, gases pressure, and $B_o$ current. These signals were acquired through two data acquisition boards. First, the NI PCI-6221 with two 16-bit analog outputs and 24 digital I/O lines (Dev1) and the NI PCIe-6351 with 16 analog inputs and 24 digital I/O lines (Dev2). Dev1 controls and acquires data from pinch valve and VCCS controllers. Dev2 controls fan heaters and RF output sequence and acquires gas pressure data. Once the signals were acquired, the data was available to LabVIEW for further analysis and software front panel (SFP) presentation.

Temperature Recording

The hyperpolarization of metabolites is temperature dependent. Thus, every circuit board designed in the inventors' lab and installed in the PHIP instrument comes with a temperature sensor. In total, there are six temperature sensors installed throughout the instrument box. In order to minimize signal noise, the temperature data acquired was further processed by LabVIEW using a Butterworth low pass digital filter with a cut off frequency at 100 Hz.

Pinch Valve System

The control of sample and gas flow was accomplished using modified Cole-Palmer 12 VDC two-way normally closed solenoid pinch valves, as described in greater detail herein above. A disposable 1¼" OD tubing was used for the sterile manipulation of gas and sample throughout the system (FIG. 15). Each pinch valve was controlled and monitored using Dev1 through a controller circuit designed in the inventors lab. This controller was designed to minimize pinch valve heating and stray magnetic fields.

Gases Pressure Recording

A Honeywell MLH150PGL06B gas pressure sensor was used to monitor nitrogen, hydrogen, and reaction chamber gas pressures. This pressure sensor is an all metal amplified sensor with temperature compensation with a range of 0 bar to 10 bar.

$B_o$ Current Recording

Figure 24:
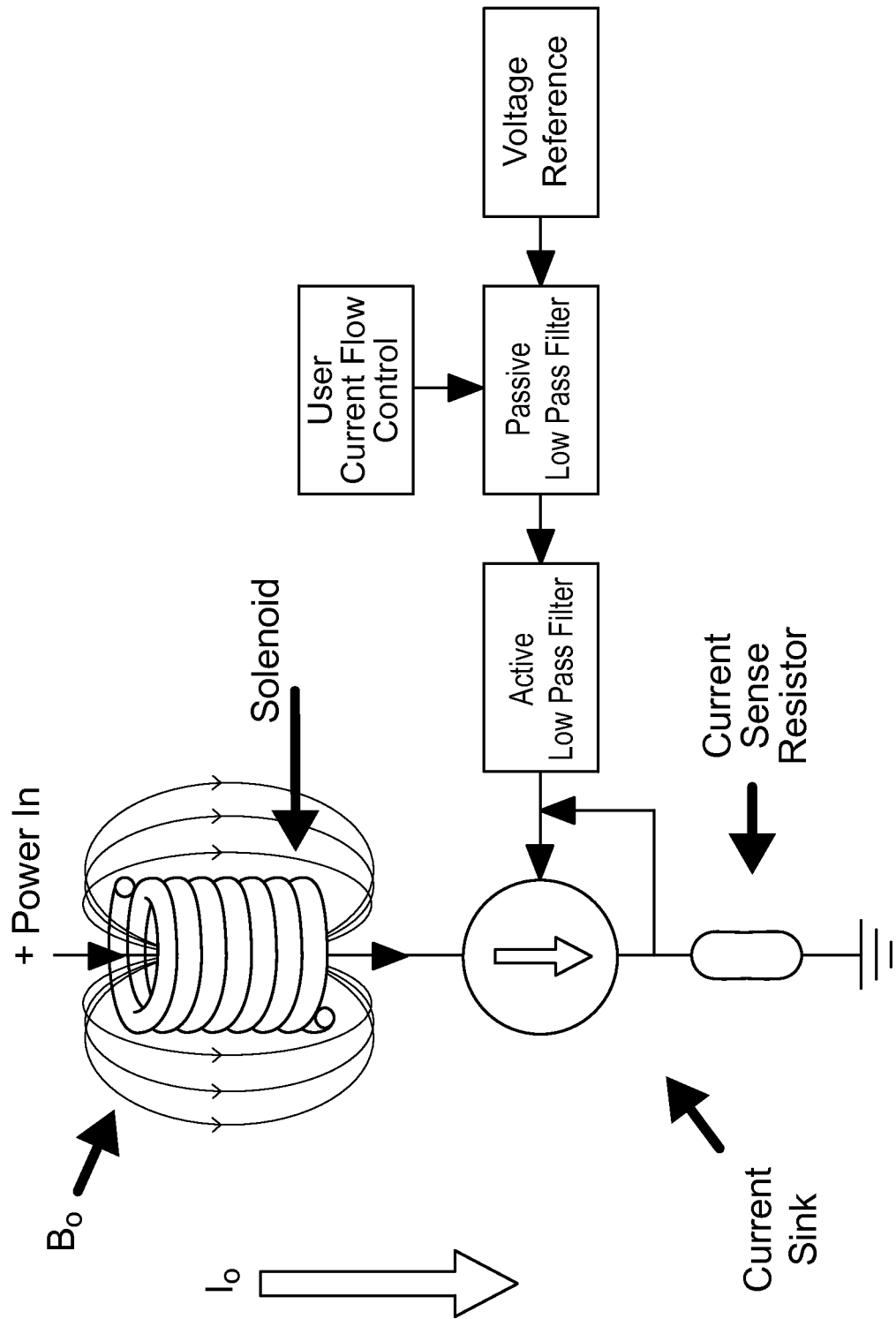
FIG. 24 depicts, in accordance with an embodiment of the invention, a voltage controlled current source (VCCS) board (Ctrlr). This board was designed in the inventors' laboratory and provides the solenoid with a stable current source. In addition, the board produces two voltage outputs, temperature and a voltage proportional to the current flowing through the solenoid.

The hyperpolarization of a $^{13}C$ based metabolite is sensitive to shifts in the $^{13}C$ resonance frequency, or Larmor Frequency (eq.3). Therefore, the monitoring of the hyperpolarization solenoid's magnetic field ($B_o$) is of the utmost importance. Exciting a metabolite sample with an incorrect RF sequence frequency will lead to poor polarization results. The Larmor Resonance Frequency is measured indirectly through a voltage measurement provided by a current controller board (designed in the inventors' laboratory). Moreover, the voltage data (V) is collected using Dev2 (FIG. 24). The derivation of the Larmor Frequency is as follows:

a) The current (I) flowing through the solenoid is given by Ohm's Law (eq.1)
b) The solenoid's $B_o$ is given by eq.2
c) The $^{13}C$ Larmor Frequency is given by eq.3
d) Inserting eq.1 into eq.2 and its result into eq.3, leads to the Larmor Resonance Frequency (ω) eq.4

$$I = \frac{V}{R} \tag{1}$$

Where V is the voltage and I is the current.

$$B_o = \mu * n * I \tag{2}$$

Where $B_o$ is the solenoid's magnetic field strength, µ is the permeability in air, n is the turn density, and I is the current.

$$\omega = -\gamma * B_o \tag{3}$$

Where ω is the Larmor Frequency in radians, γ is $^{13}C$ gyromagnetic ratio, $B_o$ is the solenoid's magnetic field magnitude.

$$\omega = -\gamma * \mu * n * \frac{V}{R} \tag{4}$$

Signal Generation

The signal outputs generated in this project are Hydrogen ($^1H$) and $^{13}C$ RF pulses. These signals are produced by Dev2's with a 2.86 MS/s analog output. The output waveforms are sequences built in advance and stored in Technical Data Management Streaming (TDMS) file format for later retrieval. The main program reads these TDMS files and when instructed, sends the data to the output RF coil around the instrument's reaction mix capsule. The TDMS file contains data on the sequence's sampling rate, waveform amplitudes and length. The sequences shape and length are dictated by the type of hyperpolarizing sequence used.

Software Design—

In this PHIP instrument prototype, the inventors used LabVIEW as a platform for acquiring, controlling, and processing data leading to the hyperpolarization of metabolites.

Software Structure—

Figure 25:
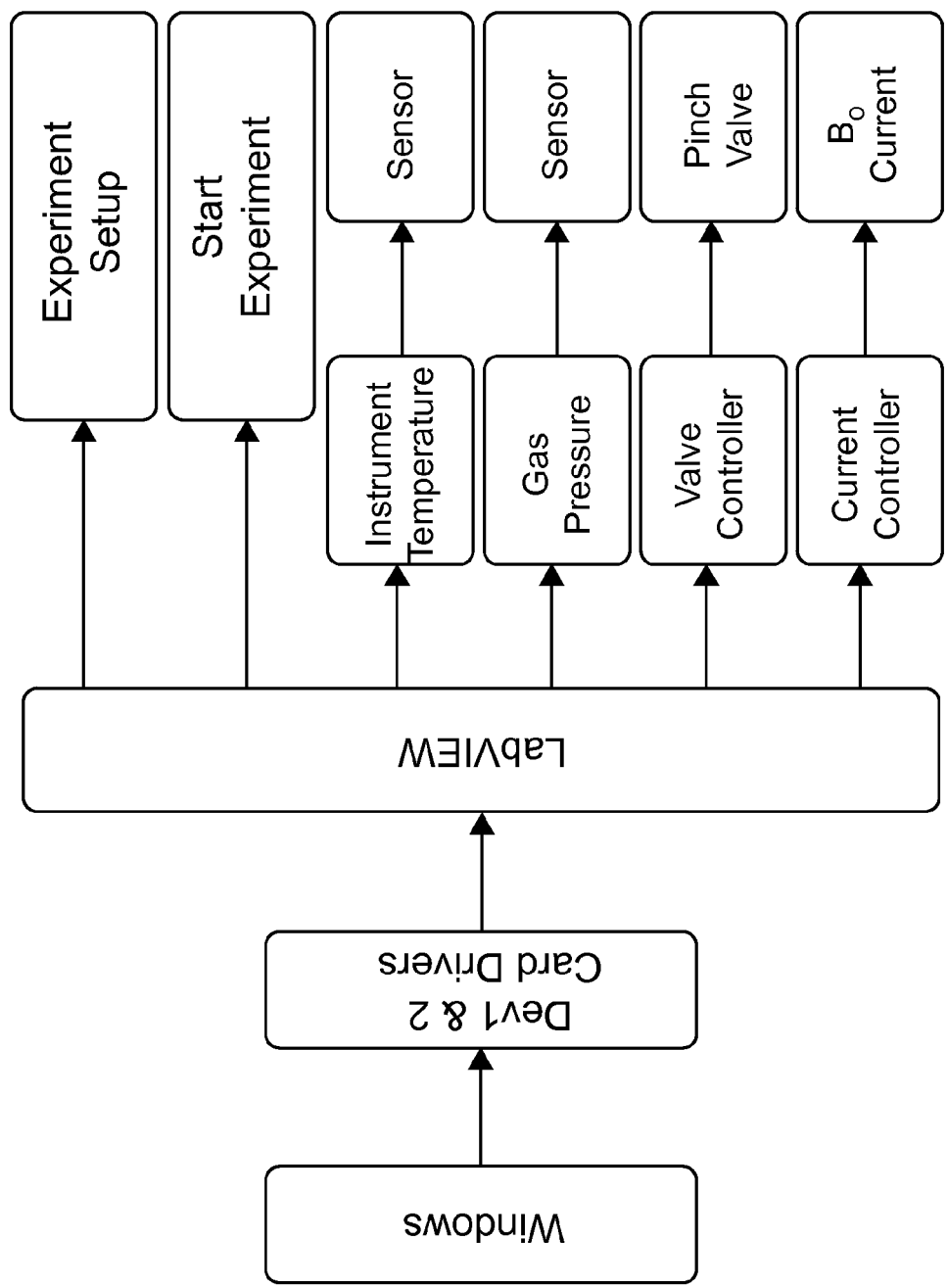
FIG. 25 depicts, in accordance with an embodiment of the invention, PHIP Instrument software structure.

The software structure of an inventive PHIP instrument is shown in FIG. 25. With 46 controls and 36 indicators on the SFP, the program is too large for linear programming. Instead, the program is event driven, allowing for more efficient program execution. Each button and knob control on the SFP is linked to an event. When a button or knob is changed by the user, an event is triggered executing different program sections. If no event is triggered, the event timer times out at 100 ms and collects gases pressure, magnetic field current, and instrument temperature data. The events available are start experiment, individual pinch valve control, and tab control setup. At time out, the following events are available; gas pressures, $B_o$ voltage drop, and instrument temperature.

Start Experiment—

The GUI developed using LabVIEW allows for control over timing on every pinch valve, simmer time (sample heating), number of gas line purges, RF sequence execution timing, experiment time range, RF sequence used, and RF feedback.

Gas Pressures—

The optimal hyperpolarization of a metabolite is dependent (among other parameters) on pressure. Thus, when the event timer times out, the software collects voltage data from pressure sensors connected at the $N_2$ and para-$H_2$ tanks, and reaction chamber using Dev1. The data is then displayed in a graph on the SFP. These results are collected at 10 Samples/Sec.

$B_o$ Voltage Drop—

The spin transfer from para-$H_2$ to $^{13}C$ nuclei is dependent on exciting the nuclei at the proper Larmor Frequency ($\omega$). Thus, when the software event timer times out, the software collects voltage data from the current controller board designed in our laboratory using Dev2 (FIG. 24). Then, the software calculates the current through the solenoid, the w for the given current (eq.3), and displays the results in a graph on the SFP.

Instrument Temperature—

In order to obtain a precursor full hydrogenation during the hyperpolarization process, the instrument environment temperature needs to be between 40° C. to 60° C. Using Dev1, the software collects data from six different parts in the instrument. Five pinch valve controller boards and a current controller board developed in the inventors' laboratory have a temperature sensor. These sensors provide temperature data from inside the instrument box. When the event timer times out, the data is collected and displayed on a graph on the SFP.

Hyperpolarization Experiment Software Structure—

Figure 26:
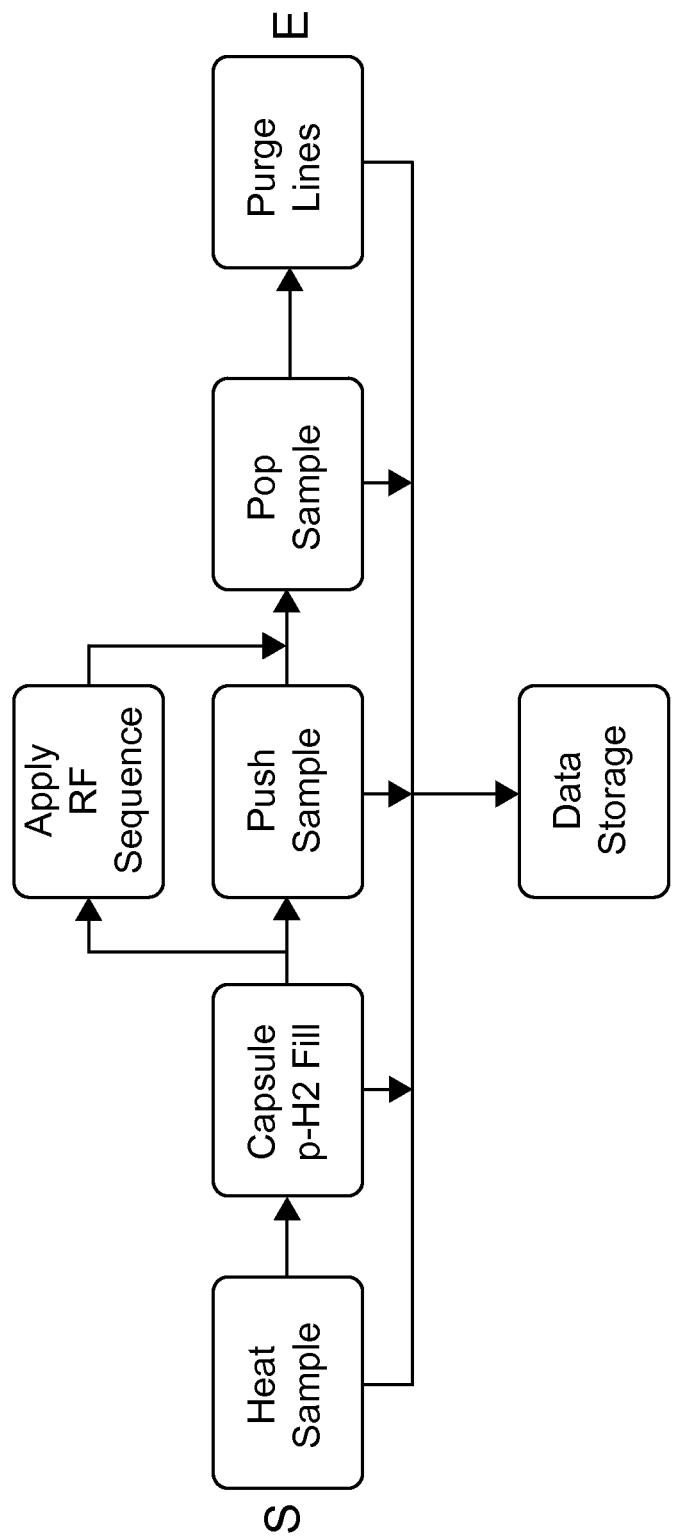
FIG. 26 depicts, in accordance with an embodiment of the invention, PHIP method experiment software structure, from start (S) to end (E).

A metabolite hyperpolarization experiment begins by heating up the sample and filling up the reaction capsule with para-$H_2$. Next, the sample is pushed into the reaction capsule and a previously chosen RF sequence applied. Then, the sample is pushed into an external vial and the lines purged (FIG. 26).

Heating Sample—

Heating sample or simmer time. This is the time the sample needs to reach proper hyperpolarization temperature.

Purging Lines—

Number of line purges after every experiment. Sample lines are purged using $N_2$ gas, while the reaction chamber is purged with para-$H_2$ gas.

$H_2$ Gas Fill—

The injection of $H_2$ gas into the reaction capsule for precursor hydrogenation.

Push Sample—

The sample is pushed into the reaction chamber.

Apply RF Sequence—

The RF sequence is used to irradiate the sample in the reaction chamber.

Pop Sample—

Once the sample has been polarized, the sample is pushed out of the reaction chamber into a vial.

Data File—

Data on simmering time, pinch valves timing, RF sequence used, gases pressure, $B_o$ current, temperature, and number of purges is stored in a TDMS file for later analysis.

SFP—

A LabVIEW front panel is composed of controls and indicators. Controls simulate instrument input devices and supply data to the program. Indicators simulate instrument output devices and display data, using either plots or LED's. The combination of controls and indicators provides the user with an intuitive GUI. This SFP is composed of four sections; Pinch Valve Indicators, Experiment Timing Setup, a series of various controls and indicators in a Tab Control setup, and a System Status Bar (FIG. 27).

Pinch Valve Indicators—

These indicators display the on/off status of the Pinch valves.

Experiment Timing Setup—

This section contains all the timing controls for the hyperpolarization of metabolites, such as; sample simmer time, pinch valve switching, RF Sequence start time, number of para-$H_2$ purges, and experiment length.

Tab Control Setup—

This control style is an excellent way to include a large number of individual controls and indicators in a small space. The Tab Control works by displaying a set of tabs for different sets of controls and indicators. In this case, the Tab Controls consists of nine tabs: Individual Controls—Pinch Valve control, RF Feedback—graphs the RF sequence sent to the reaction capsule, Output Wave—Selects a RF sequence to irradiate a sample, Pressure Plots—Graphs gases pressure, Analog Pressure—Uses dial indicators to show pressure, Temperature Plot—Graphs temperature throughout the instrument, Bo Current—graphs the current flowing through the solenoid, Sequences—Selects the RF sequences to hyperpolarize a sample.

System Status Bar—

This indicator displays the program progress status as different tasks are executed.

Experiments

Four different tests were performed: pressure, temperature, RF pulses, and experiment timing. To test pressure, the para-$H_2$ and $N_2$ gas pressure readings on the SFP were compared against a reference analog pressure gauge installed at the tanks' pressure regulator. To test temperature, the six temperature readings on the SFP were compared against an Agilent 34411A multimeter using a 1KΩ Resistance Temperature Detector (RTD) with 4-wire connection. For RF pulse delivery, the delivery of the pulse sequence by Dev2 was validated by placing an oscilloscope at the RF coil and verifying the waveform multiple amplitudes, frequency, and length. Finally, for experimental timing, para-$H_2$ and $N_2$ gas tanks were set to 2 bar, and a 10 ml water sample in a syringe was prepared. The experiment timing controls for sample heating, pinch valves, and RF sequence were setup as in FIG. 27. Then, the Start Experiment button on the SFP was pressed and the sample injected in the instrument. Next, the sample automated manipulation was timed with a timer and visually checked for the proper on/off pinch valve sequence.

Results

Pressure—The $N_2$, para-$H_2$, and reaction chamber gas pressures readings on the SFP were compared to a reference analog gauge. The readings were taken from 0 to 5 bar in 0.5 bar increments. The three pressure experiments resulted in an average of ±0.2 bar nonlinearity with respect to the reference. However, the instrument's pressure sensors have a Honeywell pressure sensor used has a ±0.25% full scale accuracy and a 2% total error over a −40 C to 125 C range.

Temperature—The six temperature sensors showed ±0.5° C. nonlinearity and a maximum ±2.1° C. difference between readings. The large difference between readings is caused by thermal Eddy currents between sensors and the RTD used as reference. With respect to experiment timing, the pinch valve sequence was measured with a hand held timer to ±100 ms resolution, resulting in a maximum deviation of ±300 ms. Finally, with regard to sequence delivery, the RF square pulses were measured $\bar{x}$=50.3422 ms with an $\sigma$=0.7 µs, and a Frequency $\bar{x}$=72.987 KHz with a $\sigma$=100 Hz.

Conclusion

The use of LabVIEW to control PHIP instrumentation is an excellent option for aiding in the maximum polarization levels of different metabolites with high reliability and at an affordable price. In addition, the use of LabVIEW for the automation of metabolite hyperpolarization improves the instrument accuracy, shortens development time, and decreases hardware costs. The operational test described herein shows that the LabVIEW-based hyperpolarization instrumentation system is stable and reliable, crucial aspects for metabolite hyperpolarization.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A device for parahydrogen induced polarization, comprising:
   (1) a reactor, comprising a first reactor inlet, a second reactor inlet, and a reactor outlet;
   (2) a precursor receiving tube, comprising a first precursor receiving tube end and a second precursor receiving tube end, wherein the first precursor receiving tube end is mechanically connected to the first reactor inlet;

(3) a parahydrogen receiving tube, comprising a first parahydrogen receiving tube end and a second parahydrogen receiving tube end, wherein the first parahydrogen receiving tube end is mechanically connected to the second reactor inlet;
(4) an outlet tube, comprising a first outlet tube end and a second outlet tube end, wherein the first outlet tube end is mechanically connected to the reactor outlet;
(5) a radio frequency (RF) coil enveloping the reactor along the vertical axis thereof;
(6) a solenoid coil enveloping the RF coil along the vertical axis thereof; and
(7) a metal heating block, comprising a longitudinal axis comprising a plurality of grooves situated perpendicular thereto, wherein each of the plurality of grooves are configured to accommodate a section of the precursor receiving tube, and wherein the section of the precursor receiving tube is wrapped around the grooves of the metal heating block.

2. The device of claim 1, further comprising one or more pinch valves rated at 25 PSI to be functional at pressures up to 100 PSI, wherein the pinch valves are configured to compress one or more segments of one or more of the precursor receiving tube, the parahydrogen receiving tube and the outlet tube.

3. A device for parahydrogen induced polarization, comprising:
(1) a reactor, comprising a first reactor inlet, a second reactor inlet, and a reactor outlet;
(2) a precursor receiving tube, comprising a first precursor receiving tube end and a second precursor receiving tube end, wherein the first precursor receiving tube end is mechanically connected to the first reactor inlet;
(3) a parahydrogen receiving tube, comprising a first parahydrogen receiving tube end and a second parahydrogen receiving tube end, wherein the first parahydrogen receiving tube end is mechanically connected to the second reactor inlet;
(4) an outlet tube, comprising a first outlet tube end and a second outlet tube end, wherein the first outlet tube end is mechanically connected to the reactor outlet;
(5) a radio frequency (RF) coil enveloping the reactor along the vertical axis thereof;
(6) a solenoid coil enveloping the RF coil along the vertical axis thereof;
(7) one or more pinch valves, wherein the pinch valves are configured to compress one or more segments of one or more of the precursor receiving tube, the parahydrogen receiving tube and the outlet tube; and
(8) a metal heating block comprising a longitudinal axis comprising a plurality of grooves situated perpendicular thereto, wherein each of the plurality of grooves are configured to accommodate a section of the precursor receiving tube, wherein the section of the precursor receiving tube is wrapped around the grooves of the metal heating block, and wherein the metal heating block is heated by conduction.

4. The device of claim 1 or 3, wherein the solenoid coil further comprises end-ring loops and mid-ring loops comprised of wire, and wherein the wire is configured to increase center field homogeneity compared to a solenoid coil without the end-ring loops and the mid-ring loops.

5. The device of claim 1, further comprising a fan situated below the metal heating block.

6. The device of claim 2 or 3, further comprising electronic components configured to control one or more of (1) one or more of the valves of the system, (2) the solenoid coil and (3) the RF coil.

7. The device of claim 6, wherein the operation of the electronic components is controlled by software.

8. The device of claim 7, wherein the software is configured with instructions for the device to generate an RF transfer pulse sequence with excitation at a first bandwidth corresponding to a hydrogen nuclei and a second bandwidth corresponding to a hyperpolarizable nuclei, when the instructions are executed.

9. The device of claim 8, wherein the hyperpolarizable nuclei is $^{13}C$ or $^{15}N$.

10. The device of claim 9, wherein the software includes instructions for the device to generate the RF transfer pulse sequence based on three required scalar coupling constants, comprising $J_{1H\text{-}2H}$, $J_{1H\text{-}X}$ and $J_{2H\text{-}X}$, wherein X comprises a hyperpolarizable nuclei.

\* \* \* \* \*